United States Patent
Shimoyama

(10) Patent No.: US 12,303,328 B2
(45) Date of Patent: May 20, 2025

(54) ULTRASONIC ENDOSCOPE AND DISTAL END UNIT THEREOF

(71) Applicant: FUJIFILM Corporation, Tokyo (JP)

(72) Inventor: Yuto Shimoyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 147 days.

(21) Appl. No.: 18/336,022

(22) Filed: Jun. 16, 2023

(65) Prior Publication Data

US 2023/0329671 A1 Oct. 19, 2023

Related U.S. Application Data

(63) Continuation of application No. PCT/JP2021/047234, filed on Dec. 21, 2021.

(30) Foreign Application Priority Data

Jan. 12, 2021 (JP) .................. 2021-002650

(51) Int. Cl.
| | | |
|---|---|---|
| A61B 8/00 | (2006.01) | |
| A61B 1/06 | (2006.01) | |
| A61B 1/267 | (2006.01) | |
| A61B 8/12 | (2006.01) | |

(52) U.S. Cl.
CPC .............. *A61B 8/12* (2013.01); *A61B 1/06* (2013.01); *A61B 1/2676* (2013.01); *A61B 8/445* (2013.01)

(58) Field of Classification Search
CPC ...................................... A61B 8/12
See application file for complete search history.

(56) References Cited

U.S. PATENT DOCUMENTS

| | | |
|---|---|---|
| 5,499,630 A | 3/1996 | Hiki et al. |
| 9,332,961 B2 | 5/2016 | Ogawa |
| 9,775,589 B2 | 10/2017 | Hashiguchi et al. |
| 2019/0090857 A1 | 3/2019 | Yamamoto et al. |
| 2020/0333580 A1 | 10/2020 | Igarashi |

FOREIGN PATENT DOCUMENTS

| | | |
|---|---|---|
| JP | H07143985 | 6/1995 |
| JP | 2000354597 | 12/2000 |
| JP | 2002306489 | 10/2002 |
| JP | 2008253489 | 10/2008 |
| WO | 2012067010 | 5/2012 |
| WO | 2015114995 | 8/2015 |
| WO | 2018003322 | 1/2018 |
| WO | 2019155665 | 8/2019 |

OTHER PUBLICATIONS

"International Search Report (Form PCT/ISA/210) of PCT/JP2021/047234," mailed on Feb. 22, 2022, with English translation thereof, pp. 1-5.
"International Preliminary Report on Patentability (Form PCT/IPEA/409) of PCT/JP2021/047234," mailed on Oct. 26, 2022, with English translation thereof, pp. 1-6.

*Primary Examiner* — Joseph M Santos Rodriguez
(74) *Attorney, Agent, or Firm* — JCIPRNET

(57) ABSTRACT

An ultrasonic endoscope includes: a distal end part body provided on a distal end side of an insertion part; and an ultrasound transducer provided on a distal end side of the distal end part body, in which an outer peripheral surface of the distal end part body is improved to increase a contact region of a proximal end part of the ultrasound transducer with a patient's body wall surface, so that it is possible to reliably perform visualization of an ultrasound image in the proximal end part.

17 Claims, 15 Drawing Sheets

ULTRASONIC ENDOSCOPE AND DISTAL END UNIT THEREOF

CROSS-REFERENCE TO RELATED APPLICATIONS

The present application is a Continuation of PCT International Application No. PCT/JP2021/047234 filed on Dec. 21, 2021 claiming priority under 35 U.S.C § 119(a) to Japanese Patent Application No. 2021-002650 filed on Jan. 12, 2021. Each of the above applications is hereby expressly incorporated by reference, in its entirety, into the present application.

BACKGROUND OF THE INVENTION

1. Field of the Invention

The present invention relates to an ultrasonic endoscope and a distal end unit thereof.

2. Description of the Related Art

As an ultrasonic endoscope, an ultrasonic endoscope that comprises an electronic scanning type ultrasound transducer (also referred to as an ultrasound oscillator array and an ultrasound unit) in a distal end hard part (distal end unit) configuring a distal end part of an insertion part of an endoscope is known. The ultrasonic endoscope uses a puncture needle led out from a treatment tool outlet port of the distal end hard part through a treatment tool channel and inserted into a lesion part to perform treatment, such as collecting a cellular tissue of the lesion part, while acquiring an ultrasound image of the lesion part (an observation site, a test site, an examination site, or the like can also be used) using the ultrasound transducer. For example, in collecting a cellular tissue of a lymph node of a bronchus, treatment of puncturing into the lymph node with the puncture needle is performed while acquiring an ultrasound image of the lymph node with the ultrasonic endoscope.

In observing the lymph node via ultrasonic waves, in a case where there is a gap between the ultrasound transducer and a bronchial wall surface, since the ultrasonic wave is not transmitted through air, an image of the lymph node is not obtained. For this reason, to acquire a clear ultrasound image of the lymph node without using a balloon, there is a need for bringing the ultrasound transducer into close contact with the bronchial wall surface.

JP2002-306489A discloses an ultrasonic endoscope in which an angle between a center line of an ultrasonic scanning range (effective angle) and a major axis (longitudinal axis) of a distal end hard part is defined such that ultrasonic scanning can be performed in a lymph node at any of a position close to and a position away from a bronchial wall surface.

JP2000-354597A discloses an ultrasonic endoscope in which, for the same purpose as the invention described in JP2002-306489A, a distal end part of a distal end hard part attached with an ultrasound transducer is tilted forward (inclined) to a side opposite to a side on which an outlet port of a treatment tool (puncture needle or the like) is formed. WO2012/067010A and JP1995-143985A (JP-H7-143985A) disclose an ultrasonic endoscope in which, to improve insertability or to reduce insertion force of a puncture needle, a distal end part of a distal end hard part is tilted forward similarly to the invention described in JP2000-354597A.

SUMMARY OF THE INVENTION

In the insertion part of the ultrasonic endoscope and a distal end hard part thereof, a further reduction in diameter is achieved to reduce a burden on a patient and to improve insertability. Note that, in reducing the diameter of the distal end hard part, visualization of an ultrasound image by a proximal end part of the ultrasound transducer, that is, an end part close to an outlet port from which the puncture needle (treatment tool) is led out, is important in a procedure of the ultrasonic endoscope. In this case, while a contact region of the proximal end part of the ultrasound transducer with respect to the bronchial wall surface needs to be increased, there is no disclosure or suggestion about this point in the respective patent documents described above.

Here, in the ultrasonic endoscope described in JP2000-354597A, WO2012/067010A, and JP1995-143985A (JP-H7-143985A), since the distal end part of the distal end hard part is tilted forward, the proximal end part of the ultrasound transducer easily comes into contact with the bronchial wall surface. Note that, even in this case, it is not certain whether or not a region where the proximal end part of the ultrasound transducer comes into contact with the bronchial wall surface is increased, depending on a forward tilt angle of the distal end part of the distal end hard part.

The distal end part of the distal end hard part protrudes outward with respect to an outer periphery of the proximal end part depending on the above-described forward tilt angle, and there may be an influence on operability, such as the insertability of the insertion part. In addition, an area for electrical wiring of the ultrasound transducer also needs to be secured.

In a case where only the distal end part of the distal end hard part is tilted forward, since a protrusion angle of the puncture needle with respect to a visualization surface of the ultrasound transducer is an acute angle, a puncture depth of the puncture needle with respect to the lymph node is increased. As a result, puncture into the lymph node, which was previously possible, may be made impossible. To maintain a relative angle of the ultrasound transducer and the puncture needle, an angle of a pipe line for a treatment tool provided in the distal end part needs to be moderated. In this case, since the distal end part is extended, there may be an influence on operability, such as the insertability of the insertion part.

The present invention has been accomplished in view of such a situation, and an object of the present invention is to provide an ultrasonic endoscope and a distal end unit thereof capable of reliably performing visualization of an ultrasound image in a proximal end part of an ultrasound transducer.

To attain the object of the present invention, there is a provided an ultrasonic endoscope comprising a distal end part body provided on a distal end side of an insertion part, and an ultrasound transducer provided on a distal end side of the distal end part body, in which an outer peripheral surface of the distal end part body includes a first surface that is provided on a proximal end side of the ultrasound transducer and that extends along a longitudinal axis of the insertion part, a second surface that is provided on a proximal end side of the first surface and that extends along the longitudinal axis, the second surface being positioned on a one direction side of a first direction perpendicular to the longitudinal axis with respect to the first surface, and a stepped surface that connects the proximal end side of the first surface and a distal end side of the second surface, and in a case where a direction perpendicular to both the longitudinal axis and the first direction is referred to as a second direction, an angle indicating an irradiation range of an ultrasonic wave emitted from the ultrasound transducer in a case where the distal end part body is viewed from a second direction side is referred to as an effective angle, and an intersection of a tangent line in contact with the ultrasound transducer and in contact with the stepped surface at a position closest to the one direction side and the ultrasound transducer is referred to as a first intersection, the first intersection is included in a range of 1/3 on a proximal end side of the effective angle. It is preferable that the first intersection is included in a range of 1/4 on the proximal end side of the effective angle.

With the ultrasonic endoscope, since a contact region of a proximal end part of the ultrasound transducer with a wall surface can be increased, it is possible to reliably perform visualization of an ultrasound image in the proximal end part.

There is provided the ultrasonic endoscope according to another aspect of the present invention further comprising an outlet port that is provided in the outer peripheral surface of the distal end part body and that is opened on the one direction side, and from which a treatment tool is led out, a pipe line that is connected to the outlet port in the distal end part body and into which the treatment tool is inserted, and an observation window of an observation optical system provided in the stepped surface, in which a second intersection that is an intersection of a center line of a distal end part of the pipe line connected to the outlet port and the tangent line is positioned on a proximal end side of the distal end part body with respect to the first intersection in a case where the distal end part body is viewed from the second direction side. As a result, the treatment tool led out from the outlet port can be observed with the observation optical system.

In the ultrasonic endoscope according to still another aspect of the present invention, the second intersection is positioned between the ultrasound transducer and the stepped surface. As a result, the treatment tool led out from the outlet port can be observed with the observation optical system.

There is provided the ultrasonic endoscope according to still another aspect of the present invention further comprising an outlet port that is provided in the outer peripheral surface of the distal end part body and that is opened on the one direction side, and from which a treatment tool is led out, and a pipe line that is connected to the outlet port in the distal end part body and into which the treatment tool is inserted, in which an angle between the longitudinal axis and a distal end part of the pipe line is 20° to 35° in a case where the distal end part body is viewed from the second direction side. As a result, operability, such as insertability of the ultrasonic endoscope, is ensured, and an increase in load applied from the treatment tool to the pipe line is prevented.

In the ultrasonic endoscope according to still another aspect of the present invention, the distal end part of the pipe line has a first distal end part that is connected to the outlet port, and a second distal end part that is provided on a proximal end side of the first distal end part, and in a case where the distal end part body is viewed from the second direction side, a first angle between the longitudinal axis and the first distal end part is 20° to 35°, and a second angle between the longitudinal axis and the second distal end part is 5° to 20° and is an angle smaller than the first angle. As a result, operability, such as insertability of the ultrasonic endoscope, is ensured, and an increase in load applied from the treatment tool to the pipe line is prevented.

In the ultrasonic endoscope according to still another aspect of the present invention, an angle between a center line of the effective angle and the distal end part of the pipe line is 15° to 60° in a case where the distal end part body is viewed from the second direction side. As a result, it is possible to insert the treatment tool at an appropriate angle with respect to a visualization surface of the ultrasound transducer.

In the ultrasonic endoscope according to still another aspect of the present invention, an observation window of an observation optical system is provided in the stepped surface, and the ultrasound transducer is included in a visual field range of the observation optical system. As a result, contact of the ultrasound transducer with a wall surface can be observed with the observation optical system.

In the ultrasonic endoscope according to still another aspect of the present invention, a center point of the observation window is positioned on the one direction side with respect to the ultrasound transducer in a case where the distal end part body is viewed from the second direction side. As a result, contact of the ultrasound transducer with a wall surface can be observed with the observation optical system.

In the ultrasonic endoscope according to still another aspect of the present invention, an observation window of an observation optical system and an illumination window of an illumination optical system are provided in the stepped surface.

There is provided the ultrasonic endoscope according to still another aspect of the present invention further comprising an outlet port that is opened in the first surface and from which a treatment tool is led out, and an observation window of an observation optical system provided in the stepped surface. As a result, the treatment tool led out from the outlet port can be observed with the observation optical system.

In the ultrasonic endoscope according to still another aspect of the present invention, the distal end part body includes an ultrasonic attachment part to which the ultrasound transducer is attached, a first surface forming part that is provided on a proximal end side of the ultrasonic attachment part and that has the first surface, a body part that is provided on a proximal end side of the first surface forming part and that has the second surface, and a protruding portion that is provided in at least the ultrasonic attachment part and that protrudes to the other direction side opposite to the one direction side with respect to the body part. As a result, since it is possible to tilt forward only the ultrasound transducer with respect to the longitudinal axis without tilting forward the distal end part or the whole distal end part body with respect to the longitudinal axis, it is possible to ensure the insertability of the distal end part body (insertion part).

In the ultrasonic endoscope according to still another aspect of the present invention, an outlet port from which a treatment tool is led out is opened in the first surface, and the protruding portion is formed from an opening region of the outlet port to a distal end side of the ultrasonic attachment part in a case where the distal end part body is viewed from the second direction side.

In the ultrasonic endoscope according to still another aspect of the present invention, the protruding portion has inclined surfaces of two stages or more having different inclination angles with respect to the longitudinal axis from a proximal end side toward a distal end side of the protruding portion in a case where the distal end part body is viewed from the second direction side, and the inclination angles of the inclined surfaces gradually decrease toward the distal end side of the protruding portion. As a result, a burden on a patient is reduced.

In the ultrasonic endoscope according to still another aspect of the present invention, an outlet port from which a treatment tool is led out is opened in the first surface, and a position in the first direction of the outlet port and a position of an apex in the first direction of the ultrasound transducer are aligned in a case where the distal end part body is viewed from the second direction side. A clearance is reliably secured between a distal end of the treatment tool led out from the outlet port and the ultrasound transducer.

In the ultrasonic endoscope according to still another aspect of the present invention, the distal end part body includes an ultrasonic attachment part to which the ultrasound transducer is attached, a first surface forming part that is provided on a proximal end side of the ultrasonic attachment part and that has the first surface and an outlet port of a treatment tool formed in the first surface, and a body part that is provided on a proximal end side of the first surface forming part and that has the second surface, and a width in the second direction of the ultrasonic attachment part is formed to be smaller than a width in the second direction of the first surface forming part in a case where the distal end part body is viewed from a first direction side. As a result, it is possible to reduce the size of the ultrasonic attachment part to improve insertability.

There is provided the ultrasonic endoscope according to still another aspect of the present invention further comprising a connecting inclined surface that connects the proximal end side of the ultrasonic attachment part and a distal end side of the first surface forming part.

To attain the object of the present invention, there is provided a distal end unit of an ultrasonic endoscope including a distal end part body provided on a distal end side of an insertion part of the ultrasonic endoscope, and an ultrasound transducer provided on a distal end side of the distal end part body, in which an outer peripheral surface of the distal end part body includes a first surface that is provided on a proximal end side of the ultrasound transducer and that extends along a longitudinal axis of the insertion part, a second surface that is provided on a proximal end side of the first surface and that extends along the longitudinal axis, the second surface being positioned on a one direction side of a first direction perpendicular to the longitudinal axis with respect to the first surface, and a stepped surface that connects the proximal end side of the first surface and a distal end side of the second surface, and in a case where a direction perpendicular to both the longitudinal axis and the first direction is referred to as a second direction, an angle indicating an irradiation range of an ultrasonic wave emitted from the ultrasound transducer in a case where the distal end part body is viewed from a second direction side is referred to as an effective angle, and an intersection of a tangent line in contact with the ultrasound transducer and in contact with the stepped surface at a position closest to the one direction side and the ultrasound transducer is referred to as a first intersection, the first intersection is included in a range of 1/3 on a proximal end side of the effective angle.

According to the present invention, it is possible to reliably perform visualization of an ultrasound image in the proximal end part of the ultrasound transducer.

DESCRIPTION OF THE PREFERRED EMBODIMENTS

Hereinafter, an ultrasonic endoscope 1 according to the present invention will be described with reference to the accompanying drawings.

Overall Configuration of Ultrasonic Endoscope of First Embodiment

Figure 1:
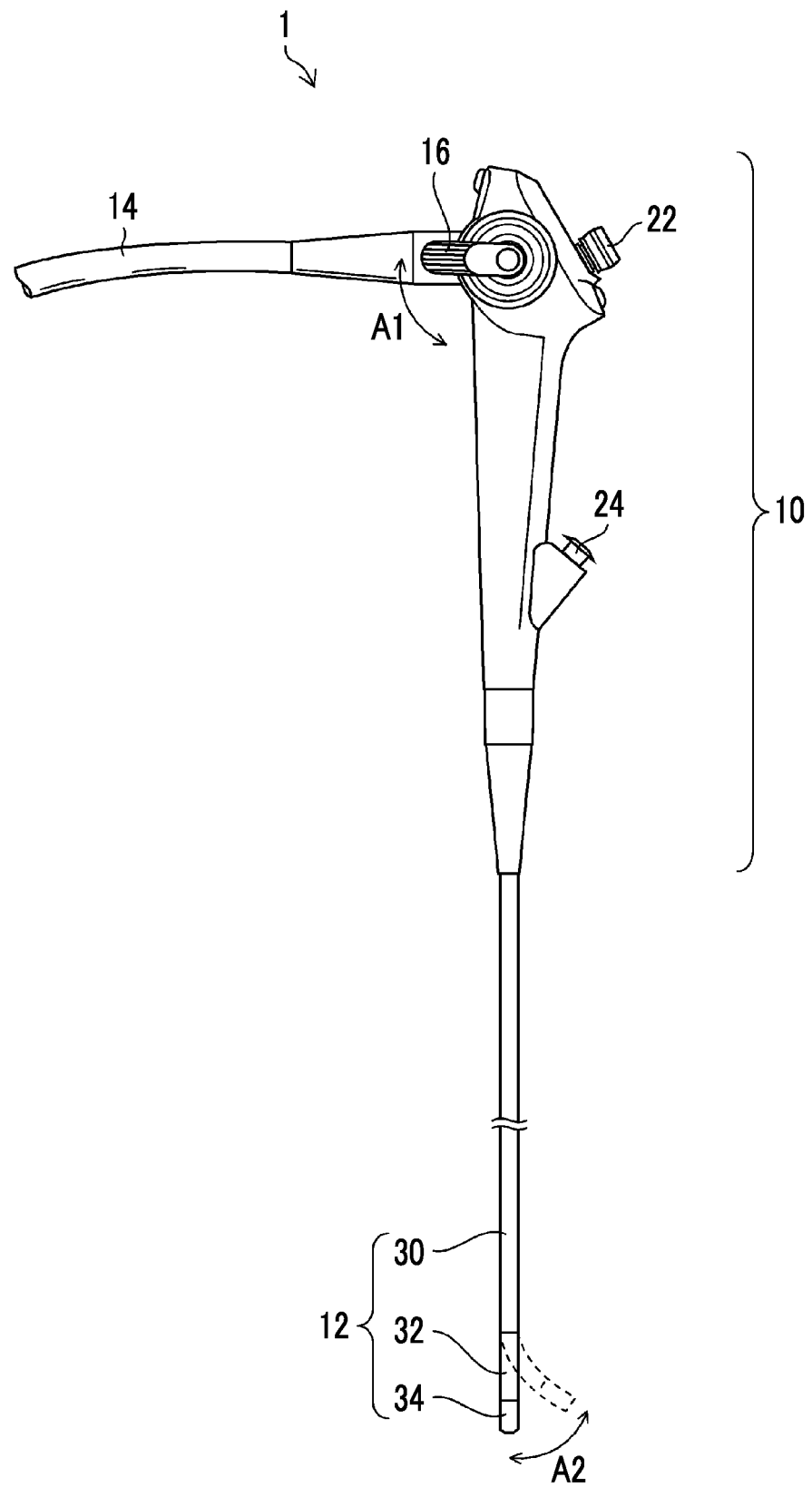
FIG. 1 is a general view of an ultrasonic endoscope (endoscope).

FIG. 1 is a general view of the ultrasonic endoscope 1. As shown in FIG. 1, the ultrasonic endoscope 1 (hereinafter, simply referred to as an "endoscope 1") is used for collection or the like of a cellular tissue of a lesion part (an observation site, a test site, or an examination site can be used). In the present embodiment, description will be provided in connection with a lymph node of a bronchus as an example of a lesion part.

The endoscope 1 is configured with an operating part 10 that is gripped by a practitioner to perform various operations, an insertion part 12 that is inserted into a body of a patient, and a universal cord 14. The endoscope 1 is connected to system constituent devices that configure an endoscope system, such as a processor device and a light source device (not shown), through the universal cord 14.

The operating part 10 is provided with various operation members that are operated by the practitioner. For example, an angle lever 16, a suction button 22, and the like of which the operations will be appropriately described below are provided.

The operating part 10 is provided with a treatment tool inlet port 24 through which a treatment tool is inserted into a treatment tool insertion channel 23 (see FIG. 4) that is inserted into the insertion part 12.

The insertion part 12 extends from a distal end of the operating part 10 and is formed in a small-diameter elongated shape as a whole. The insertion part 12 is configured with, in order from a proximal end side toward a distal end side, a soft part 30, a bendable part 32, and a distal end hard part 34 (corresponding to a distal end part body and a distal end unit of the present invention) as a distal end part.

The soft part 30 occupies most of the insertion part 12 from the proximal end side and has enough flexibility to be bent in any direction. In a case where the insertion part 12 is inserted into a body cavity, the soft part 30 is bent along an insertion path into the body cavity.

The bendable part 32 is bent in an up-down direction (A2 direction) by rotating the angle lever 16 of the operating part 10 in an A1 direction. With the bending operation of the bendable part 32, the distal end hard part 34 can be directed in a desired direction.

As will be described in detail below with reference to FIGS. 2 to 4, the distal end hard part 34 comprises an observation optical system 40 and illumination optical systems 44 that are provided to capture an observation image in the body, an ultrasound transducer 50 that acquires an ultrasound image, and an outlet port 52 from which the treatment tool inserted from the treatment tool inlet port 24 is led out.

The universal cord 14 includes signal cables 54, a signal cable 56, and light guides 58 shown in FIGS. 3 and 4 described below in detail. A connector is provided in an end portion (not shown) of the universal cord 14. The connector is connected to predetermined system constituent devices that configure the endoscope system, such as a processor device and a light source device. As a result, power, control signals, illumination light, and the like necessary for the operation of the endoscope 1 are supplied from the system constituent devices to the endoscope 1. Conversely, data of the observation image acquired by the observation optical system 40 and data of the ultrasound image acquired by the ultrasound transducer 50 are transmitted from the endoscope 1 to the system constituent devices. The observation image and the ultrasound image transmitted to the system constituent devices are displayed on a monitor, and the practitioner or the like can observe the images.

The configuration of the operating part 10 is not limited to the aspect shown in FIG. 1. A pair of angle knobs may be provided instead of the angle lever 16, and the bendable part 32 may be bent in the up-down direction and in a right-left direction by rotating a pair of angle knobs. An air/water supply button may be provided in the operating part 10, and gas, such as air, a liquid for cleaning, and the like may be supplied to the distal end hard part 34 by operating the air/water supply button.

Configuration of Distal End Hard Part of First Embodiment

Figure 2:
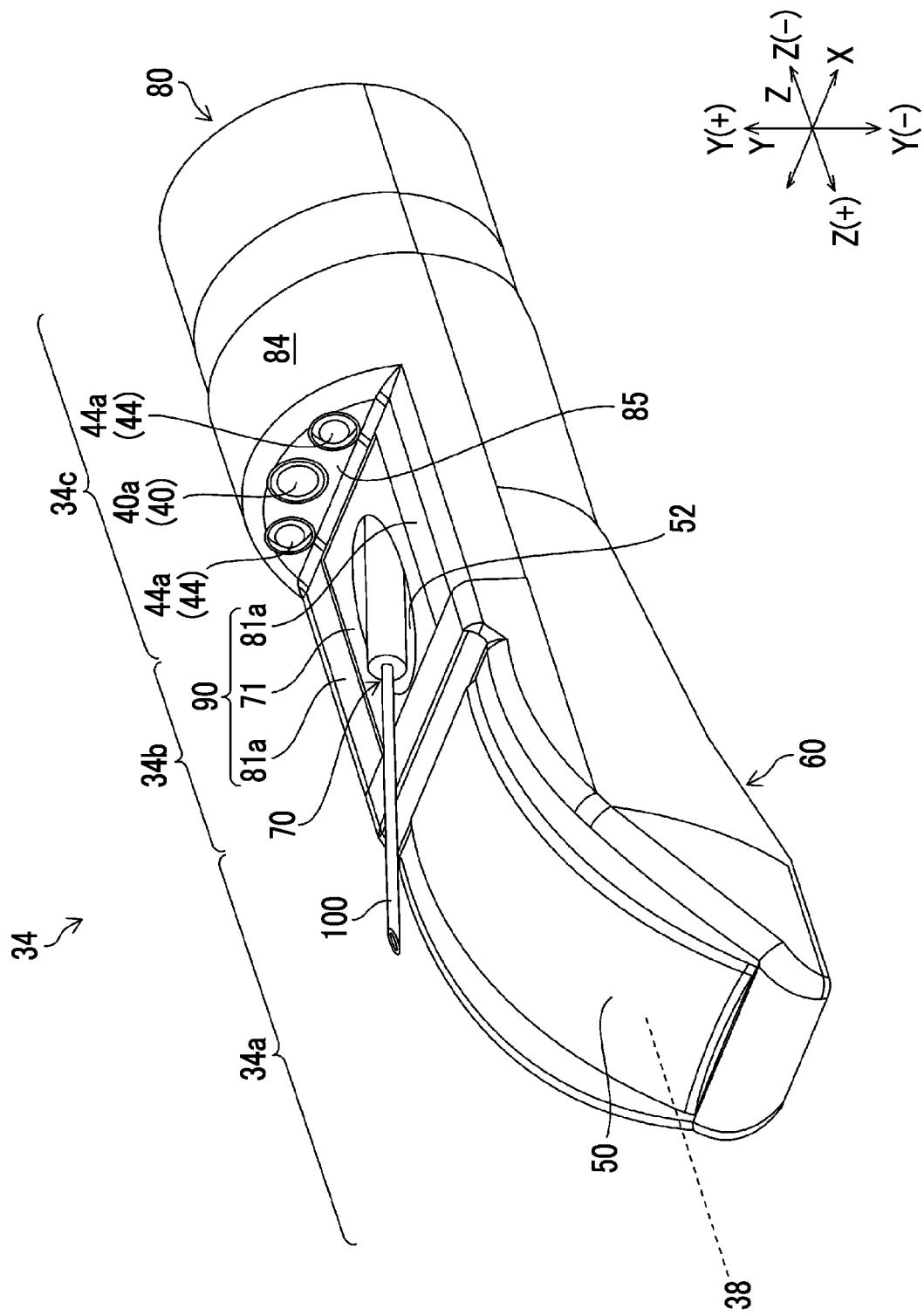
FIG. 2 is a perspective view of a distal end hard part of a first embodiment.

FIG. 2 is a perspective view of the distal end hard part 34 of the first embodiment. FIG. 3 is an exploded perspective view of the distal end hard part 34 of the first embodiment. FIG. 4 is a sectional view of the distal end hard part 34 of the first embodiment.

A Z direction in the drawing is a direction parallel to a longitudinal axis 38 of the distal end hard part 34 (insertion part 12). A Z(+) direction side of the Z direction in the drawing is a distal end side of the distal end hard part 34, and a Z(−) direction side is a proximal end side of the distal end hard part 34. A Y direction in the drawing corresponds to a first direction of the present invention perpendicular to the Z direction and is an up-down direction in each drawing in the present embodiment. A Y(+) direction side as a one direction side of the Y direction is an up direction in the drawing, and a Y(−) direction side as the other direction side opposite to the one direction side of the Y direction is a down direction in the drawing. An X direction in the drawing corresponds to a second direction of the present invention perpendicular to both the Z direction and the Y direction.

Figure 3:
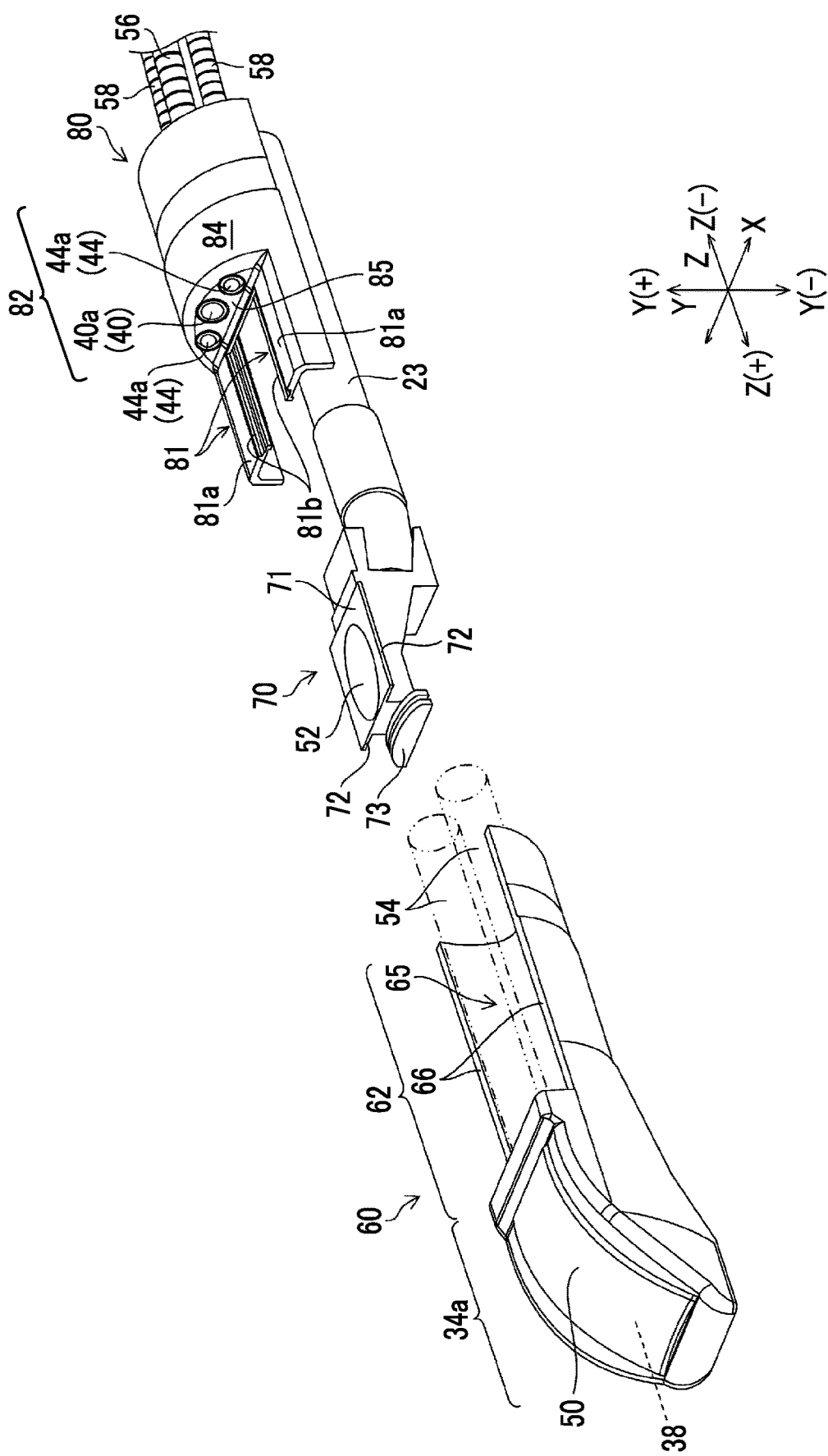
FIG. 3 is an exploded perspective view of the distal end hard part of the first embodiment.
Figure 4:
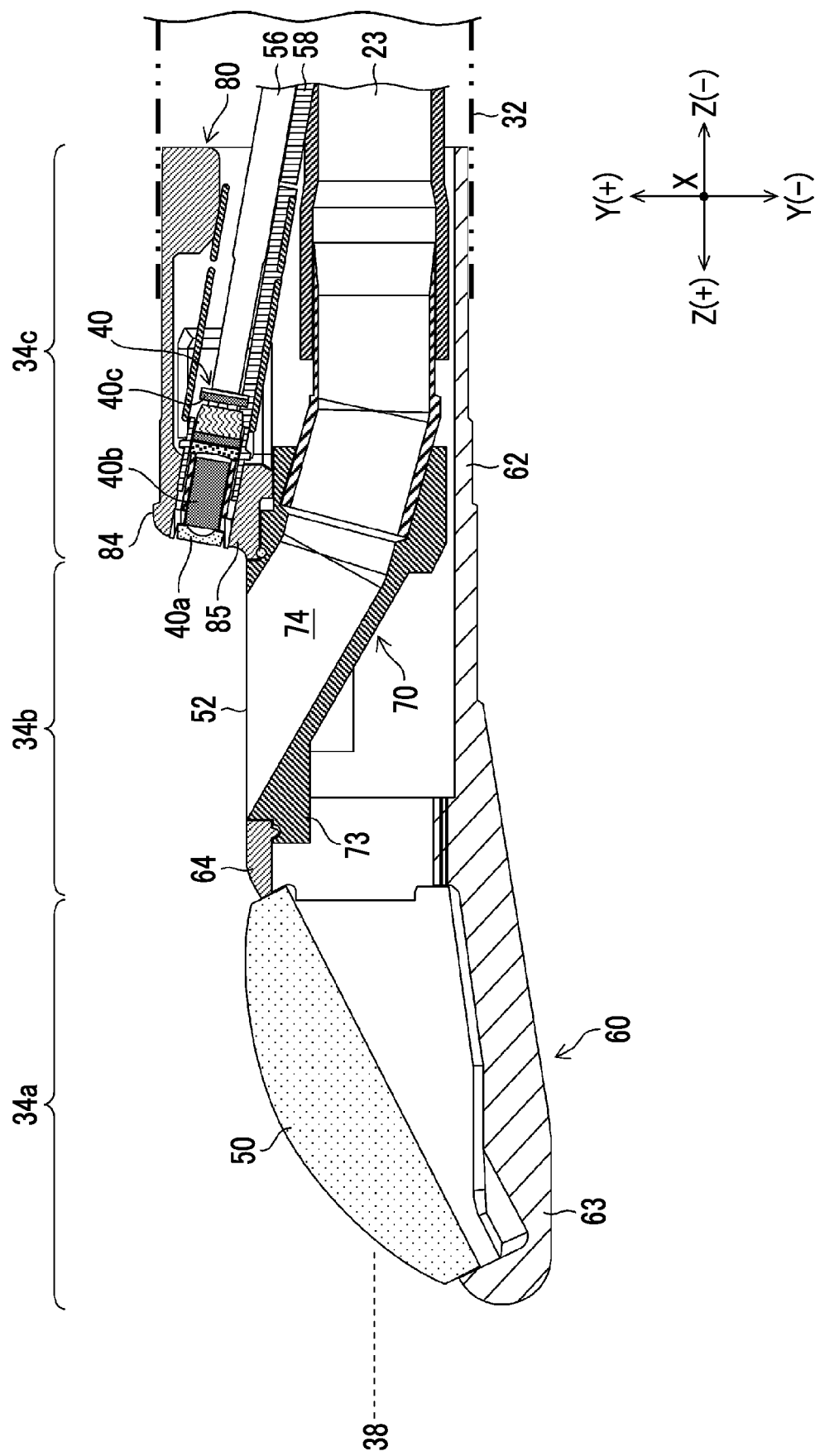
FIG. 4 is a sectional view of the distal end hard part of the first embodiment.

As shown in FIGS. 2 to 4, the distal end hard part 34 is configured by combining an ultrasound block component 60, a channel block component 70, and an optical system block component 80 (in particular, see FIG. 3). The distal end hard part 34 comprises an ultrasonic attachment part 34a, an outlet port forming part 34b (corresponding to a first surface forming part of the present invention), and a body part 34c from the distal end side toward the proximal end side of the distal end hard part 34 in a state in which the respective block components are combined (see FIGS. 2 and 4).

The ultrasound block component 60 is formed of an insulating material having insulation, and specifically, a resin material, for example, plastic, such as polysulphone and polyether imide. The ultrasound block component 60 comprises the ultrasonic attachment part 34a and an optical system block component attachment part 62 from a distal end side toward a proximal end side thereof (see FIG. 3). The ultrasonic attachment part 34a and the optical system block component attachment part 62 are formed integrally.

The ultrasound transducer 50 is attached to the ultrasonic attachment part 34a in a posture tilted forward (inclined) to the Y(−) direction side with respect to the longitudinal axis 38 in a case where the distal end hard part 34 is viewed from the X direction side (corresponding to a second direction side of the present invention). The ultrasound transducer 50 is a convex type that has an ultrasonic wave transmitting and receiving surface on which ultrasound oscillators that transmit and receive ultrasonic waves are arranged in a curved shape along a direction of the longitudinal axis 38. Data for generating an ultrasound image of a lymph node is acquired by the ultrasound transducer 50. The number of ultrasound oscillators that configure the ultrasound transducer 50 is not limited.

The optical system block component attachment part 62 extends from a region on the Y(−) direction side of the proximal end part of the ultrasonic attachment part 34a toward the proximal end side [Z(−) direction side] in a case where the distal end hard part 34 is viewed from the X direction side. A locking portion 64 that locks a locked portion 73 of the channel block component 70 described below is formed in a region on the Y(+) direction side of the proximal end part of the ultrasonic attachment part 34a (see FIG. 4). The locking portion 64 has a locking claw that configures a snap fit, for example.

The optical system block component attachment part 62 has a substantially semi-cylindrical shape corresponding to a divided part on the Y(−) direction side, that is, a divided part on a lower half side out of two divided parts obtained by dividing the outlet port forming part 34b and the body part 34c into two parts in the Y direction (into two parts vertically) (see FIG. 3). For this reason, the optical system block component attachment part 62 has an attachment part opening 65 that is opened on the Y(+) direction side.

The attachment part opening 65 is formed parallel to an XZ plane and along the Z direction. Inside the attachment part opening 65 of the optical system block component attachment part 62, the signal cables 54 that connect the ultrasound transducer 50 and the system constituent devices described above are disposed.

In the optical system block component attachment part 62, a pair of guide portions 66 that forms the attachment part opening 65 is formed, and the pair of guide portions 66 extends to the Z(−) direction side along the attachment part opening 65. The optical system block component 80 described below is attached to the pair of guide portions 66 while being slid in the Z direction. As a result, the optical system block component 80 is attached to the optical system block component attachment part 62, that is, the ultrasound block component 60, through the pair of guide portions 66.

The channel block component 70 configures the outlet port forming part 34*b* along with the optical system block component 80, and is formed of a known metal material. The channel block component 70 has the outlet port 52 of the treatment tool that is opened on the Y(+) direction side, and a substantially rectangular opening forming surface 71 parallel to the XZ plane where the outlet port 52 is opened and along the Z direction (including the longitudinal axis 38; the same applies hereinafter). In the present embodiment, description will be provided in connection with a puncture needle 100 that is used in tissue collection of a lymph node, as an example of the treatment tool.

In both end portions in the X direction of the opening forming surface 71, a pair of flange surfaces 72 parallel to the XZ plane is formed along the Z direction (see FIG. 3). The pair of flange surfaces 72 is used for attachment of the channel block component 70 to the optical system block component 80, and extends outward (X direction) from both end portions in the X direction of the opening forming surface 71.

On a distal end side of the channel block component 70, the locked portion 73 that is engaged with the locking portion 64 of the ultrasonic attachment part 34*a* is formed (see FIGS. 3 and 4). The locked portion 73 has, for example, an engagement hole with which the locking claw of the locking portion 64 is engaged.

An in-block pipe line 74 (not shown) is formed inside the channel block component 70. The in-block pipe line 74 configures a pipe line of the present invention along with the treatment tool insertion channel 23. A distal end side of the pipe line 74 is connected to the outlet port 52, and a proximal end side of the pipe line 74 is connected to the treatment tool insertion channel 23 inserted into the insertion part 12. As a result, a distal end of the puncture needle 100 inserted from the treatment tool inlet port 24 is guided to the outlet port 52 by way of the treatment tool insertion channel 23 and the pipe line 74, and is led out from the outlet port 52 to the outside.

The optical system block component 80 is formed of a resin material, like the ultrasound block component 60. The optical system block component 80 has a shape corresponding to a divided part on the Y(+) direction side (an upper half side) out of the two divided parts obtained by dividing the outlet port forming part 34*b* and the body part 34*c* into two parts in the Y direction (into two parts vertically).

The optical system block component 80 comprises, from a distal end side toward a proximal end side thereof, a pair of channel block component attachment portions 81 that is provided at an interval in the X direction, and an optical system storage portion 82 (see FIG. 3). The pair of channel block component attachment portions 81 and the optical system storage portion 82 are formed integrally.

The pair of channel block component attachment portions 81 extends from positions slightly lower than an apex on the Y(+) direction side of the optical system storage portion 82, that is, positions on the Y(−) direction side with respect to the apex, to a distal end side [Z(+) direction side] of the optical system storage portion 82 in a case where the optical system block component 80 is viewed from the X direction side.

A space for attaching the channel block component 70 is secured between the pair of channel block component attachment portions 81. In end portions on the Y(+) direction side of the pair of channel block component attachment portions 81, a pair of planes 81*a* and a pair of support surfaces 81*b* are formed (see FIG. 3). The pair of planes 81*a* has a shape parallel to the XZ plane and along the Z direction.

The pair of support surfaces 81*b* are surfaces parallel to the pair of planes 81*a*. The pair of support surfaces 81*b* are formed at positions that are positions shifted from the pair of planes 81*a* toward the above-described space and that are positions on the Y(−) direction side lower than the pair of planes 81*a* by the amount of thickness in the Y direction of the pair of flange surfaces 72.

The pair of support surfaces 81*b* supports the pair of flange surfaces 72 from both sides in the X direction. For this reason, the channel block component 70 is supported to be slidable in the Z direction between the pair of channel block component attachment portions 81 through the pair of flange surfaces 72 and the pair of support surfaces 81*b*. As a result, the channel block component 70 can be attached to the optical system block component 80 while sliding in the Z direction. Then, the channel block component 70 is adhered and fixed to the optical system block component 80.

In a case where the channel block component 70 is attached to the optical system block component 80, the opening forming surface 71 and the pair of planes 81*a* form a continuous plane 90 (corresponding to a first surface of the present invention) (see FIG. 2). The continuous plane 90 is a plane parallel to the XZ plane and along the Z direction, and configures a part of an outer peripheral surface of the distal end hard part 34. In the present embodiment, although the outlet port 52 is opened in the continuous plane 90, the outlet port 52 may be opened in surfaces (first surface) of various shapes, such as a curved surface, an inclined surface, or an uneven surface.

The optical system storage portion 82 has a substantially semi-cylindrical shape, and has a convex surface 84 and a stepped surface 85. The convex surface 84 corresponds to a second surface of the present invention, and configures a part of the outer peripheral surface of the distal end hard part 34 (optical system storage portion 82). The convex surface 84 is positioned on the Y(+) direction side with respect to the continuous plane 90 and has a shape along the Z direction. The convex surface 84 may be formed in various shapes, such as a curved surface, an inclined surface, or an uneven surface.

The stepped surface 85 is an inclined surface that connects a proximal end side of the continuous plane 90 and a distal end side of the convex surface 84, and configures a part of the outer peripheral surface of the distal end hard part 34. The inclined surface used herein includes a vertical surface having an inclination angle of 90° with respect to the Z direction.

The stepped surface 85 is provided with an observation window 40*a* of the observation optical system 40 and illumination windows 44*a* of a pair of illumination optical systems 44.

The observation optical system 40 includes the observation window 40*a* provided in the stepped surface 85, and a lens system 40*b* and an imaging element 40*c* provided in the optical system storage portion 82. The imaging element 40*c* is a charge-coupled device (CCD) type or a complementary metal oxide semiconductor (CMOS) type image sensor and captures an observation image fetched from the observation window 40*a* through the lens system 40*b*. Then, the imaging element 40*c* outputs an imaging signal of the observation image to the system constituent devices through the signal cable 56 inserted into the insertion part 12.

The illumination optical systems 44 are provided on both sides of the observation optical system 40 in the X direction, and each of the illumination optical systems 44 includes the illumination window 44a provided in the stepped surface 85, and the light guide 58 inserted into the insertion part 12. An emission end of the light guide 58 is disposed rearward of each illumination window 44a. As a result, illumination light supplied from the light source device to each light guide 58 is emitted from each illumination window 44a.

In a case where the channel block component 70 is attached to the optical system block component 80, the pair of guided portions 66 is attached to the optical system block component attachment part 62 of the ultrasound block component 60 through the pair of guide portions 66. In this case, the locking portion 64 of the ultrasonic attachment part 34a locks the locked portion 73 of the channel block component 70. As a result, the movement in the Z direction of the channel block component 70 and of the optical system block component 80 with respect to the ultrasound block component 60 is restricted, and the channel block component 70 is assembled to the ultrasound block component 60.

A distal end part of the bendable part 32 is externally fitted on and fixed to proximal end parts of both of the optical system storage portion 82 and the optical system block component attachment part 62 (see FIG. 4). As a result, the optical system storage portion 82 and the optical system block component attachment part 62 are held to be inseparable in the Y direction by the bendable part 32. As a result, the optical system block component 80 is assembled to the ultrasound block component 60.

As described above, the ultrasound block component 60, the channel block component 70, and the optical system block component 80 are combined, and the distal end hard part 34 is formed. In the distal end hard part 34, the ultrasound transducer 50, the outlet port 52, and the stepped surface 85 (observation window 40a) are disposed in order from the distal end side toward the proximal end side. That is, the outlet port 52 is disposed between the ultrasound transducer 50 and the observation window 40a. For this reason, puncture into a lymph node from a bronchial wall surface by the puncture needle 100 can be observed through the observation optical system 40.

The distal end hard part 34 of the present embodiment has a shape capable of increasing a contact region of a proximal end part on the Z(−) direction side of the ultrasound transducer 50, that is, a proximal end part on the side of the outlet port 52 from which the puncture needle 100 is led out, with a bronchial wall surface in acquiring an ultrasound image of a lymph node via the endoscope 1. Hereinafter, the shape will be specifically described.

Figure 5:
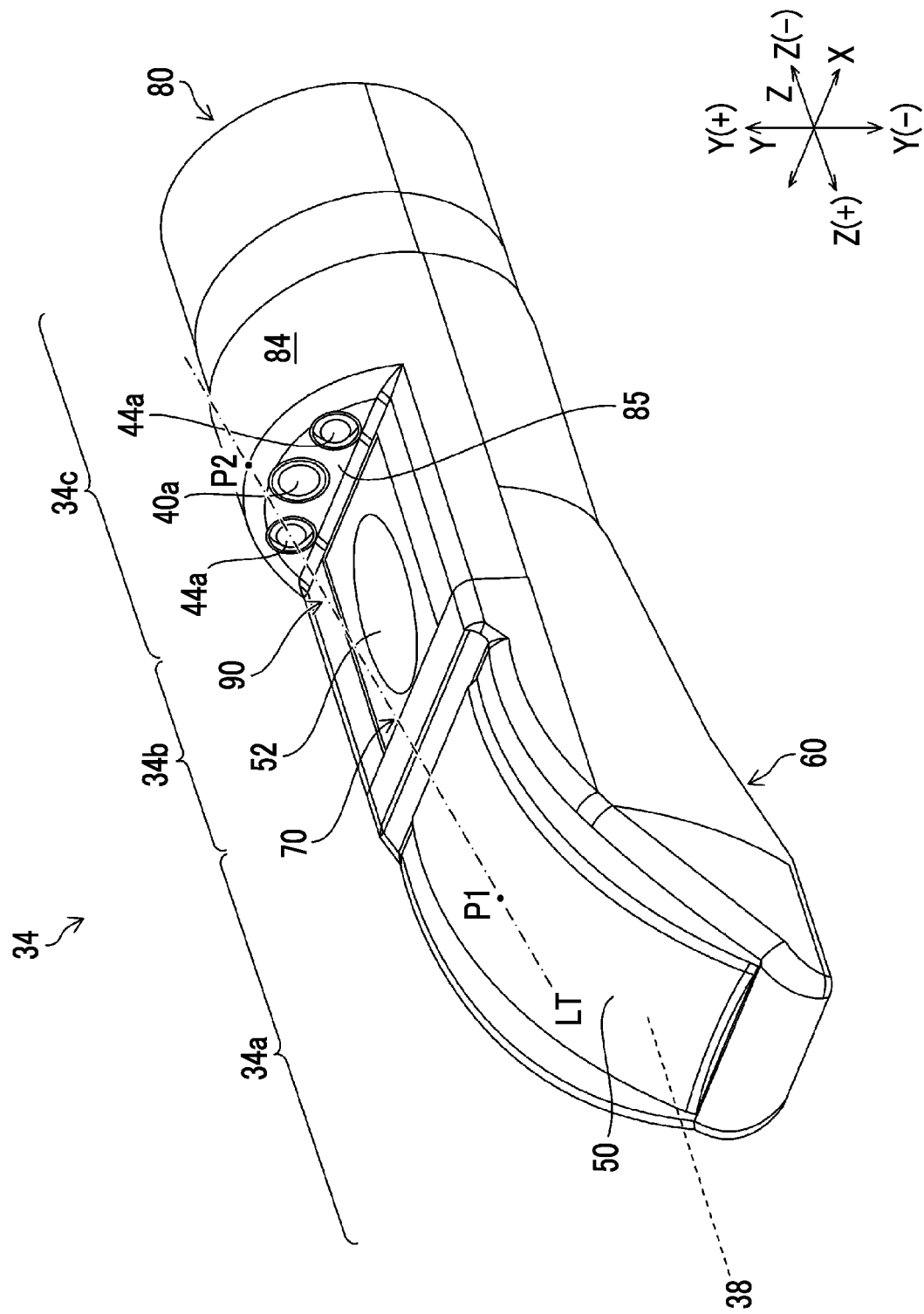
FIG. 5 is a perspective view of the distal end hard part including a tangent line.
Figure 6:
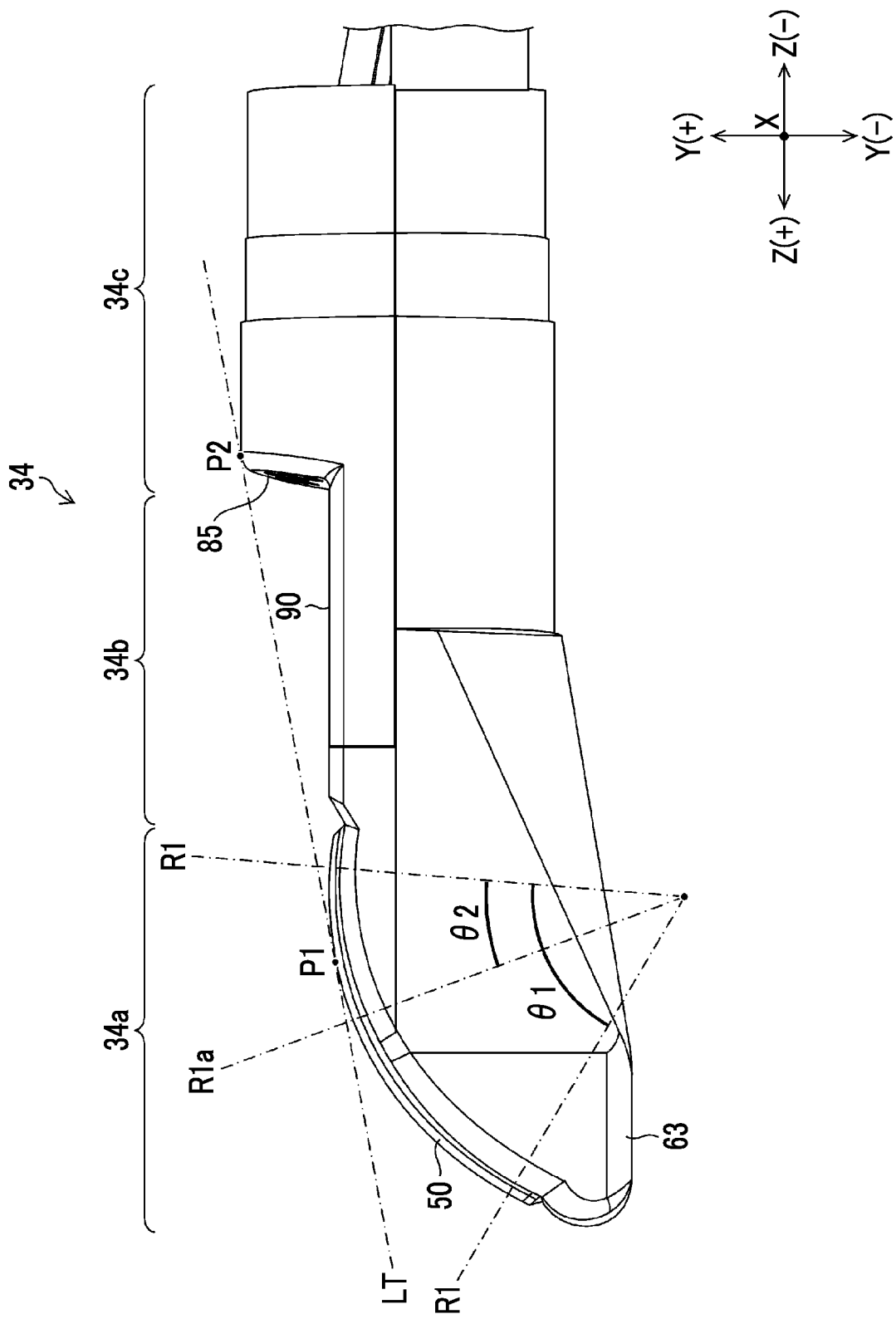
FIG. 6 is a side view of the distal end hard part including the tangent line.

FIG. 5 is a perspective view of the distal end hard part 34 including a tangent line LT. FIG. 6 is a side view of the distal end hard part 34 including the tangent line LT. As shown in FIGS. 5 and 6, in the present embodiment, the shape of the distal end hard part 34 capable of increasing the contact region of the proximal end part of the ultrasound transducer 50 with the bronchial wall surface is defined using the tangent line LT and an effective angle θ1 of the ultrasound transducer 50.

The tangent line LT is a line in contact with the ultrasound transducer 50 and in contact with the stepped surface 85 at a position (apex) closest to the Y(+) direction side. Here, a point where the tangent line LT is in contact with the ultrasound transducer 50 is referred to as a tangent point P1 (corresponding to a first intersection of the present invention), and a point where the tangent line LT is in contact with the stepped surface 85 is referred to as a tangent point P2.

The effective angle θ1 of the ultrasound transducer 50 is an angle indicating an irradiation range R1 of an ultrasonic wave emitted from the ultrasound transducer 50 in a case where the distal end hard part 34 is viewed from the X direction side. A one-dot chain line R1a in FIG. 6 indicates a boundary of a range (θ2=⅓×θ1) of ⅓ from a proximal end side [Z(−) direction side] of the effective angle θ1.

In a case where the distal end hard part 34 is viewed from the X direction side as shown in FIG. 6, and in a case where the distal end hard part 34 is brought into contact with a bronchial wall surface, as indicated by the tangent line LT, the tangent point P1 and the tangent point P2 come into contact with the bronchial wall surface. In this case, a region between the tangent point P1 and the tangent point P2 in the distal end hard part 34 is a region that has difficulty coming into contact with the bronchial wall surface, and conversely, a region on the distal end side with respect to the tangent point P1 is a region that easily comes into contact with the bronchial wall surface. For this reason, the region on the distal end side with respect to the tangent point P1 in the proximal end part of the ultrasound transducer 50 is easily brought into contact with the bronchial wall surface, and conversely, a region on the proximal end side with respect to the tangent point P1 is a region that has difficulty coming into contact with the bronchial wall surface.

Accordingly, in the present embodiment, the shape of the distal end hard part 34 is adjusted such that the tangent point P1 is included in a range (a range of an angle θ2 in the drawing) of ⅓ on the proximal end side of the effective angle θ1. The adjustment of the shape of the distal end hard part 34 includes adjustment of a shape, an attachment position, and a posture of the ultrasound transducer 50 and adjustment of a shape, a forming position, and an inclination angle of the stepped surface 85. It is preferable that the tangent point P1 is included in a range of ¼ on the proximal end side of the effective angle θ1.

The shape of the distal end hard part 34 is adjusted in this way, whereby, in a case where the distal end hard part 34 is brought into contact with the bronchial wall surface, and in a case where the distal end hard part 34 is viewed from the X direction side, a region between the one-dot chain line R1a and the tangent point P1 in the proximal end part of the ultrasound transducer 50 is reliably brought into contact with the bronchial wall surface (see FIG. 6). That is, a part of the proximal end part of the ultrasound transducer 50 is reliably brought into contact with the bronchial wall surface. As a result, the contact region of the proximal end part of the ultrasound transducer 50 with the bronchial wall surface is increased.

In addition, the shape of the distal end hard part 34 is adjusted such that the position of the tangent point P1 is further shifted to the proximal end side [Z(−) direction side], whereby the contact region of the proximal end part of the ultrasound transducer 50 with the bronchial wall surface is further increased.

As described above, in the first embodiment, the shape of the distal end hard part 34 is adjusted such that the tangent point P1 is included in the range of 1/3 on the proximal end side of the effective angle θ1 of the ultrasound transducer 50 in a case where the distal end hard part 34 is viewed from the X direction side, whereby the contact region of the proximal end part of the ultrasound transducer 50 with the bronchial wall surface is reliably increased. As a result, it is possible to reliably perform visualization of an ultrasound image of a lymph node with the proximal end part of the ultrasound transducer 50.

Second Embodiment

Next, a distal end hard part 34 of an endoscope 1 of a second embodiment of the present invention will be described. In the distal end hard part 34 of the second embodiment, a shape (angle) of the in-block pipe line 74 is adjusted to realize ensuring of operability, such as insertability of the endoscope 1, resulting from a reduction in length of the distal end hard part 34, reduction of insertion force of the puncture needle 100, and prevention of an increase in load applied from the puncture needle 100 to the channel block component 70. Since the distal end hard part 34 of the second embodiment has essentially the same configuration as the distal end hard part 34 of the first embodiment, the same elements in function or configuration as those in the above-described first embodiment are represented by the same reference numerals, and description thereof will not be repeated. Furthermore, description of the same effects as in the first embodiment will also not be repeated.

Figure 7:
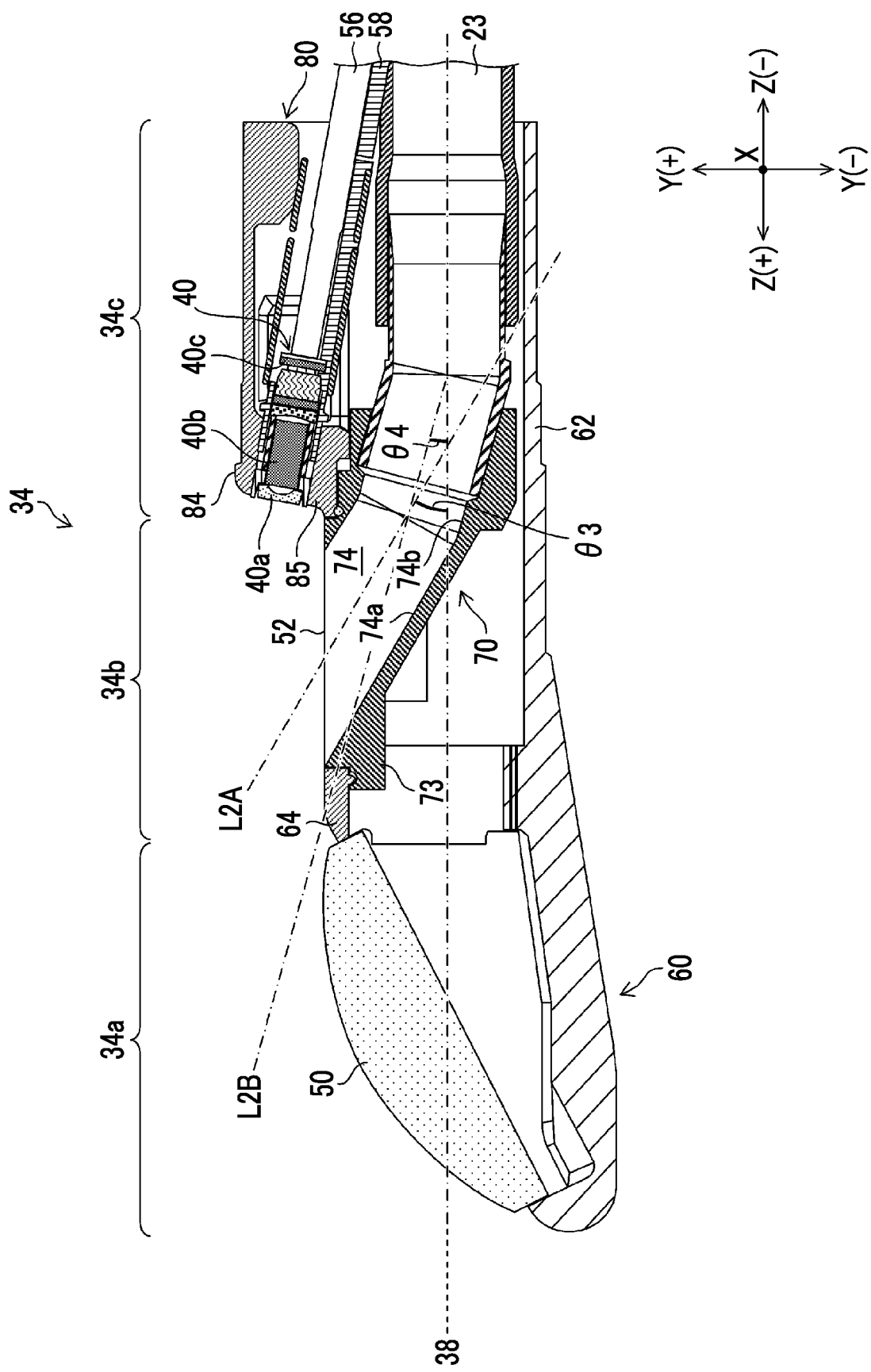
FIG. 7 is a sectional view of a distal end hard part of an endoscope of a second embodiment.

FIG. 7 is a sectional view of the distal end hard part 34 of the endoscope 1 of the second embodiment. As shown in FIG. 7, the in-block pipe line 74 has a shape bent in two stages in a case where the distal end hard part 34 is viewed from the X direction side. Specifically, the in-block pipe line 74 is configured with a first pipe line 74a and a second pipe line 74b.

The first pipe line 74a corresponds to a distal end part and a first distal end part of a pipe line of the present invention, and is connected to the outlet port 52 in the channel block component 70. The second pipe line 74b corresponds to a second distal end part of the present invention, and is provided on a proximal end side of the first pipe line 74a. A distal end part of the treatment tool insertion channel 23 is connected to the second pipe line 74b.

An angle θ3 (corresponding to a first angle of the present invention) between a center line L2A of the first pipe line 74a and the longitudinal axis 38 is set to 20° to 35°. Here, since a length of the in-block pipe line 74 from the distal end part of the treatment tool insertion channel 23 to the outlet port 52 is extended as the angle θ3 is made smaller, the distal end hard part 34 is extended, and there may be an influence on operability, such as insertability of the endoscope 1. Conversely, as the angle θ3 is made greater, a load applied from the puncture needle 100 inserted into the in-block pipe line 74 to the channel block component 70 is increased. For this reason, in the second embodiment, the angle θ3 is set to 20° to 35°.

An angle θ4 (corresponding to a second angle of the present invention) between a center line L2B of the second pipe line 74b and the longitudinal axis 38 is set to 5° to 20° and is an angle smaller than the angle θ3. In a case where the angle θ4 of the second pipe line 74b and the angle θ3 of the first pipe line 74a are made to have the same magnitude, a width in the Y direction of the in-block pipe line 74 increases, that is, a thickness in the Y direction of the distal end hard part 34 increases, to cause an increase in distal end diameter, and there may be an influence on operability, such as insertability of the endoscope 1. Accordingly, the angle θ4 of the second pipe line 74b is made smaller than the angle θ3 of the first pipe line 74a, whereby an increase in thickness in the Y direction of the distal end hard part 34 is suppressed.

As described above, in the second embodiment, the angle θ3 is set to 20° to 35°, whereby operability, such as insertability of the endoscope 1, is ensured, resulting from a reduction in length of the distal end hard part 34, and an increase in load applied from the puncture needle 100 to the channel block component 70 is prevented. The angle θ4 is set to an angle of 5° to 20° and smaller than the angle θ3, whereby operability, such as insertability of the endoscope 1, is ensured. The in-block pipe line 74 is bent in two stages, whereby it is possible to reduce insertion force of the puncture needle 100, compared to a case where the in-block pipe line 74 is bent in one stage.

Third Embodiment

Next, a distal end hard part 34 of an endoscope 1 of a third embodiment of the present invention will be described. In the distal end hard part 34 of each embodiment described above, the ultrasound transducer 50, the outlet port 52, and the stepped surface 85 (observation window 40a) are disposed from the distal end side toward the proximal end side, whereby puncture into the lymph node from the bronchial wall surface by the puncture needle 100 can be observed with the observation optical system 40.

In contrast, in the distal end hard part 34 of the third embodiment, a condition for allowing reliable observation of puncture into the lymph node described above with the observation optical system 40 is defined. Since the distal end hard part 34 of the third embodiment has essentially the same configuration as the distal end hard part 34 of each embodiment described above, the same elements in function or configuration as those in each embodiment described above are represented by the same reference numerals, and description thereof will not be repeated. Furthermore, description of the same effects as in each embodiment described above will also not be repeated.

Figure 8:
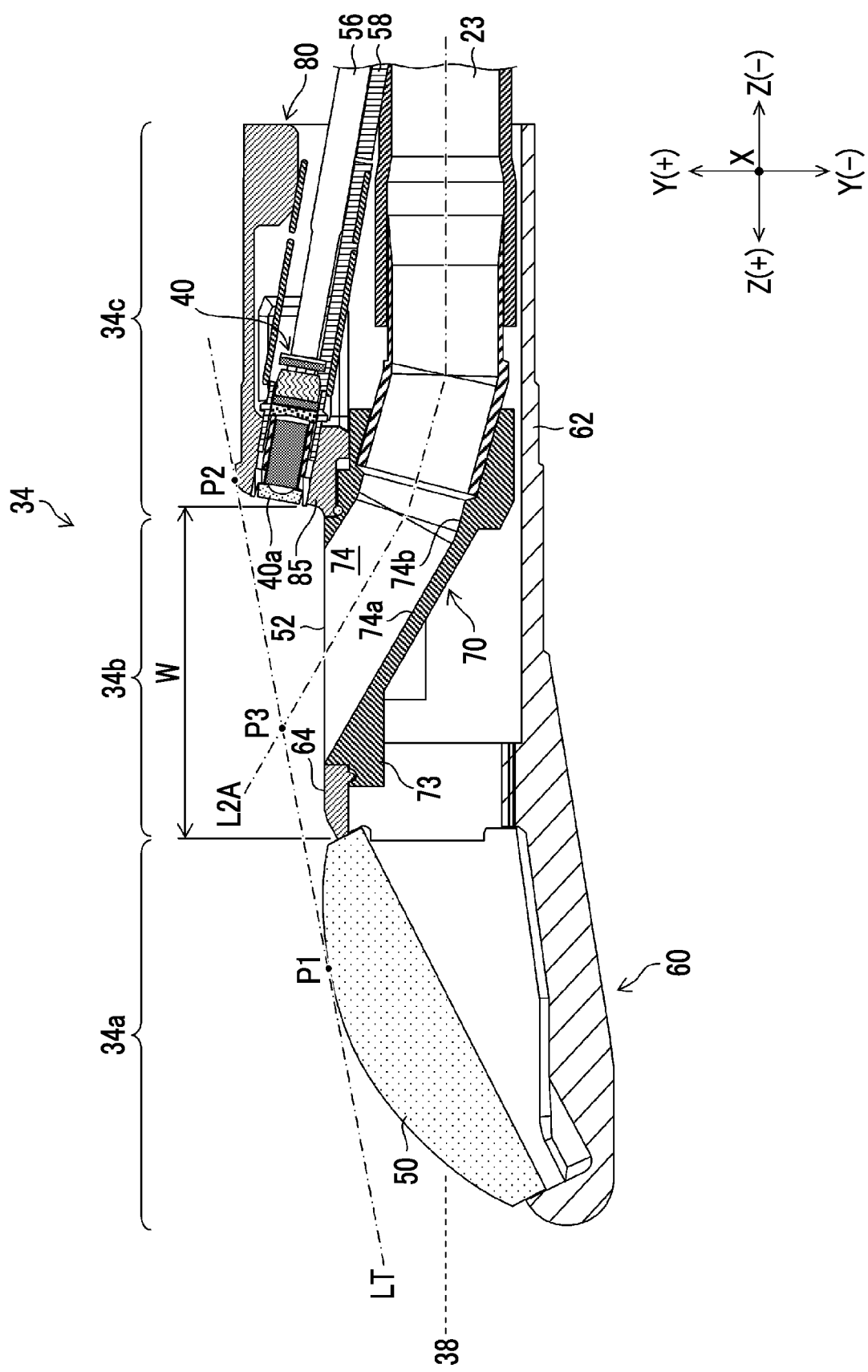
FIG. 8 is a sectional view of a distal end hard part of an endoscope of a third embodiment.

FIG. 8 is a sectional view of the distal end hard part 34 of the endoscope 1 of the third embodiment. As shown in FIG. 8, in a case where the distal end hard part 34 is viewed from the X direction side, an intersection P3 (corresponding to a second intersection of the present invention) of the tangent line LT and the center line L2A of the first pipe line 74a is positioned at a position on the proximal end side of the distal end hard part 34 with respect to the tangent point P1, and more preferably, in a range W indicating an area between the ultrasound transducer 50 and the observation window 40a. In a case where the outlet port 52 is opened on the proximal end side of the distal end hard part 34 with respect to the stepped surface 85 (observation window 40a), the intersection P3 is positioned on the proximal end side of the distal end hard part 34 with respect to the tangent point P1.

The intersection P3 corresponds to a position where the puncture needle 100 led out from the outlet port 52 starts puncture into the lymph node from the bronchial wall surface in a state in which the ultrasound transducer 50 is brought into contact with the bronchial wall surface. Then, the intersection P3 is positioned in the range W, that is, is positioned in front of the observation window 40a, whereby puncture into the lymph node from the bronchial wall surface by the puncture needle 100 can be reliably observed with the observation optical system 40.

Fourth Embodiment

Next, a distal end hard part 34 of an endoscope 1 of a fourth embodiment of the present invention will be described. The distal end hard part 34 of the fourth embodiment allows contact of the ultrasound transducer 50 with the bronchial wall surface to be observed with the observation optical system 40. Since the distal end hard part 34 of the fourth embodiment has essentially the same configuration as the distal end hard part 34 of each embodiment described above, the same elements in function or configuration as those in each embodiment described above are represented by the same reference numerals, and description thereof will not be repeated. Furthermore, description of the same effects as in each embodiment described above will also not be repeated.

Figure 9:
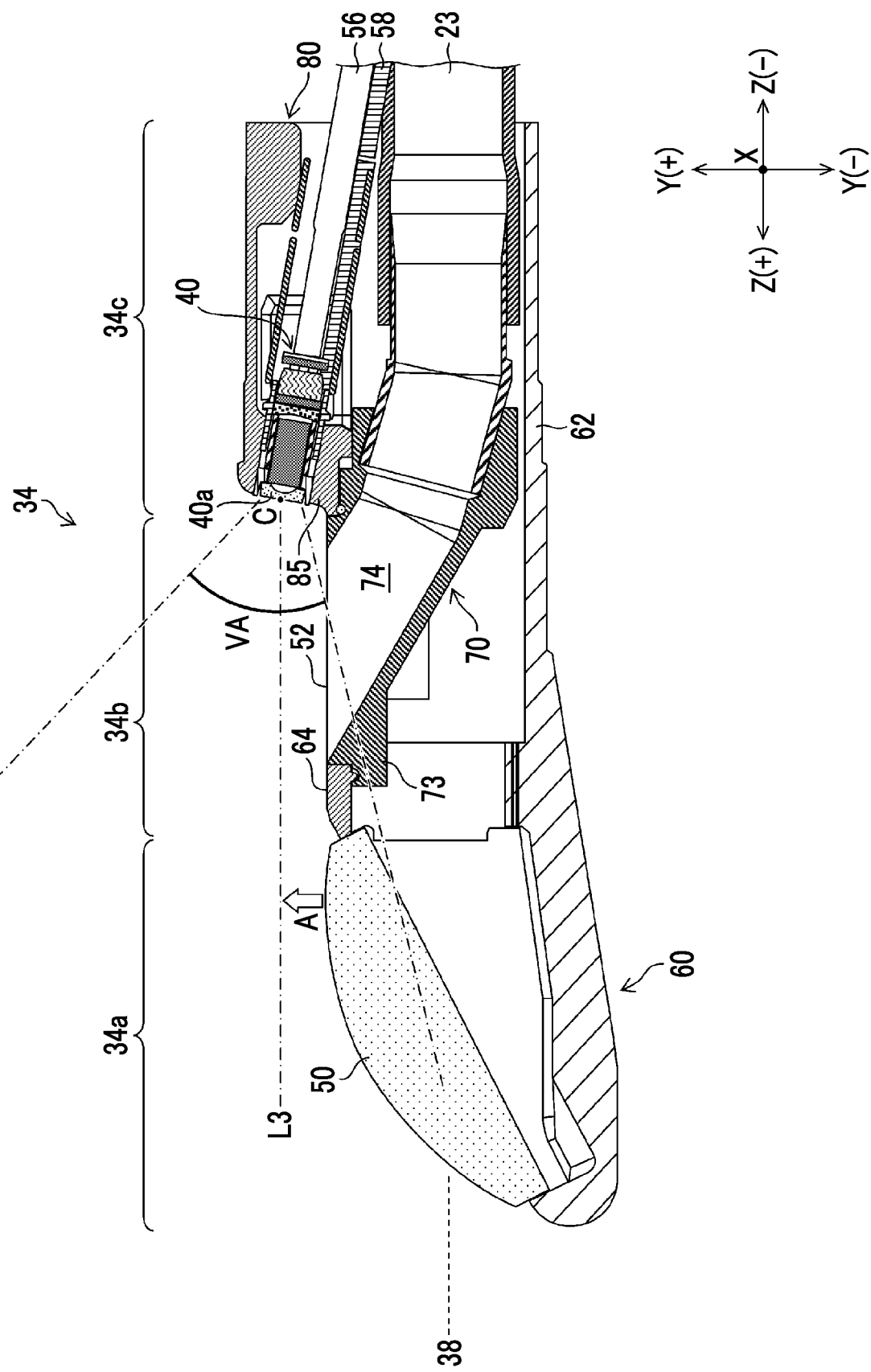
FIG. 9 is a sectional view of a distal end hard part of an endoscope of a fourth embodiment.

FIG. 9 is a sectional view of the distal end hard part 34 of the endoscope 1 of the fourth embodiment. As shown in FIG. 9, in the distal end hard part 34 of the fourth embodiment, the ultrasound transducer 50, in particular, the proximal end part thereof, is included in a visual field range of the observation optical system 40 indicated by reference numeral VA in a case of being viewed from the X direction side. As a result, contact of the ultrasound transducer 50, in particular, the proximal end part thereof, with the bronchial wall surface can be observed with the observation optical system 40.

In the distal end hard part 34 of the fourth embodiment, a center point C of the observation window 40a is positioned on the Y(+) direction side with respect to the ultrasound transducer 50 as indicated by an arrow A and a one-dot chain line L3 in the drawing in a case of being viewed from the X direction side. As a result, as described above, since the ultrasound transducer 50 can be included in the visual field range of the observation optical system 40, contact of the ultrasound transducer 50 with the bronchial wall surface can be observed.

Fifth Embodiment

Next, a distal end hard part 34 of an endoscope 1 of a fifth embodiment of the present invention will be described. The distal end hard part 34 of the fifth embodiment allows the puncture needle 100 to be inserted at an appropriate angle with respect to a visualization surface (lymph node 200) of the ultrasound transducer 50. Since the distal end hard part 34 of the fifth embodiment has essentially the same configuration as the distal end hard part 34 of each embodiment described above, the same elements in function or configuration as those in each embodiment described above are represented by the same reference numerals, and description thereof will not be repeated. Furthermore, description of the same effects as in each embodiment described above will also not be repeated.

Figure 10:
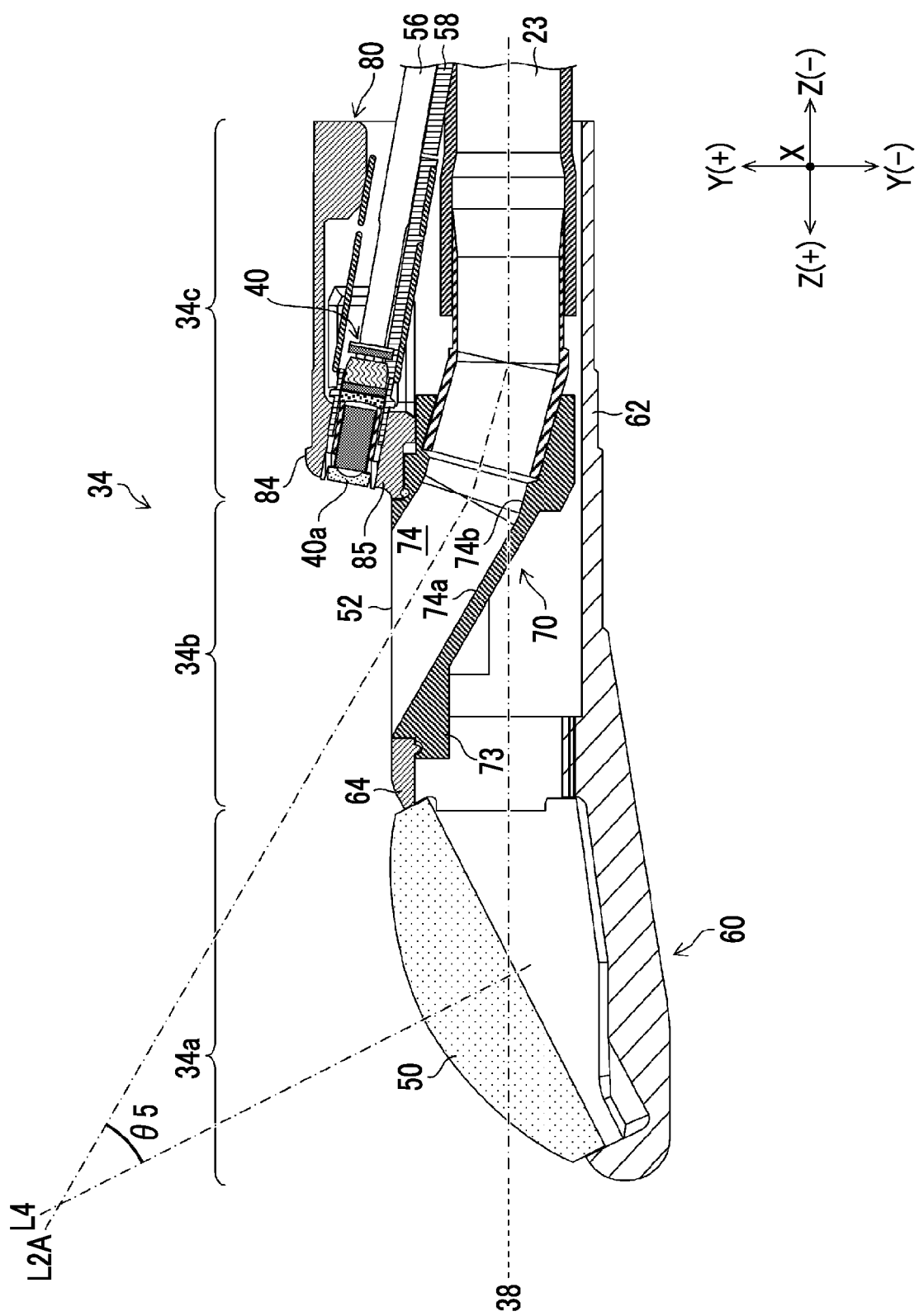
FIG. 10 is a sectional view of a distal end hard part of an endoscope of a fifth embodiment.
Figure 11:
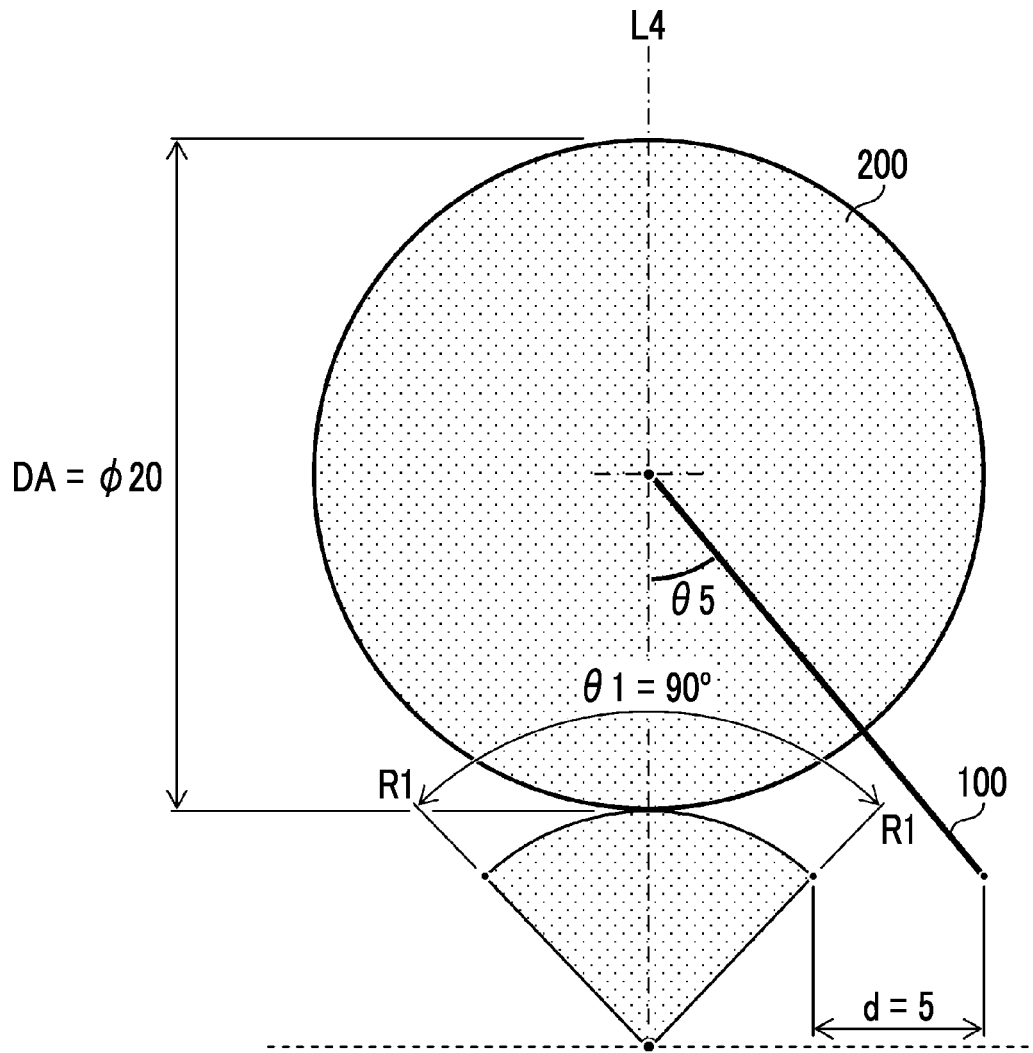
FIG. 11 is a diagram schematically showing puncture into a lymph node by a puncture needle.
Figure 11:
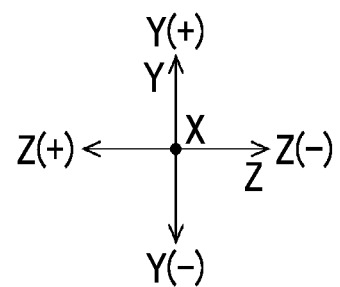

FIG. 10 is a sectional view of the distal end hard part 34 of the endoscope 1 of the fifth embodiment. FIG. 11 is a diagram schematically showing puncture into a lymph node 200 by the puncture needle 100. Reference numeral DA in FIG. 11 indicates a diameter of the lymph node 200, and here, DA is, for example, φ20 mm. Reference numeral d indicates an interval between the proximal end of the ultrasound transducer 50 and the puncture needle 100 (the center of the outlet port 52) in the Z direction, and here, d is, for example, 5 mm. In FIG. 11, the effective angle θ1 is, for example, 90°.

As shown in FIGS. 10 and 11, in the distal end hard part 34 of the fifth embodiment, the shape of the distal end hard part 34 is adjusted such that an angle θ5 between a center line L4 of the effective angle θ1 of the ultrasound transducer 50 in a case of being viewed from the X direction side and the center line L2A of the first pipe line 74a is θ5=10° to 60°. Specifically, a position posture of the ultrasound transducer 50 and the angle θ3 (see FIG. 7) of the first pipe line 74a are adjusted. As a result, since an insertion angle of the puncture needle 100 with respect to the visualization surface (lymph node 200) of the ultrasound transducer 50 can be adjusted to θ5, the insertion angle of the puncture needle 100 with respect to the visualization surface is prevented from being an acute angle or an excessively shallow angle. As a result, it is possible to insert the puncture needle 100 at an appropriate angle with respect to the visualization surface of the ultrasound transducer 50.

Sixth Embodiment

Next, a distal end hard part 34 of an endoscope 1 of a sixth embodiment of the present invention will be described. In the distal end hard part 34 of the sixth embodiment, the insertability of the distal end hard part 34 is ensured, and a burden on a patient is reduced. Since the distal end hard part 34 of the sixth embodiment has essentially the same configuration as the distal end hard part 34 of each embodiment described above, the same elements in function or configuration as those in each embodiment described above are represented by the same reference numerals, and description thereof will not be repeated. Furthermore, description of the same effects as in each embodiment described above will also not be repeated.

Figure 12:
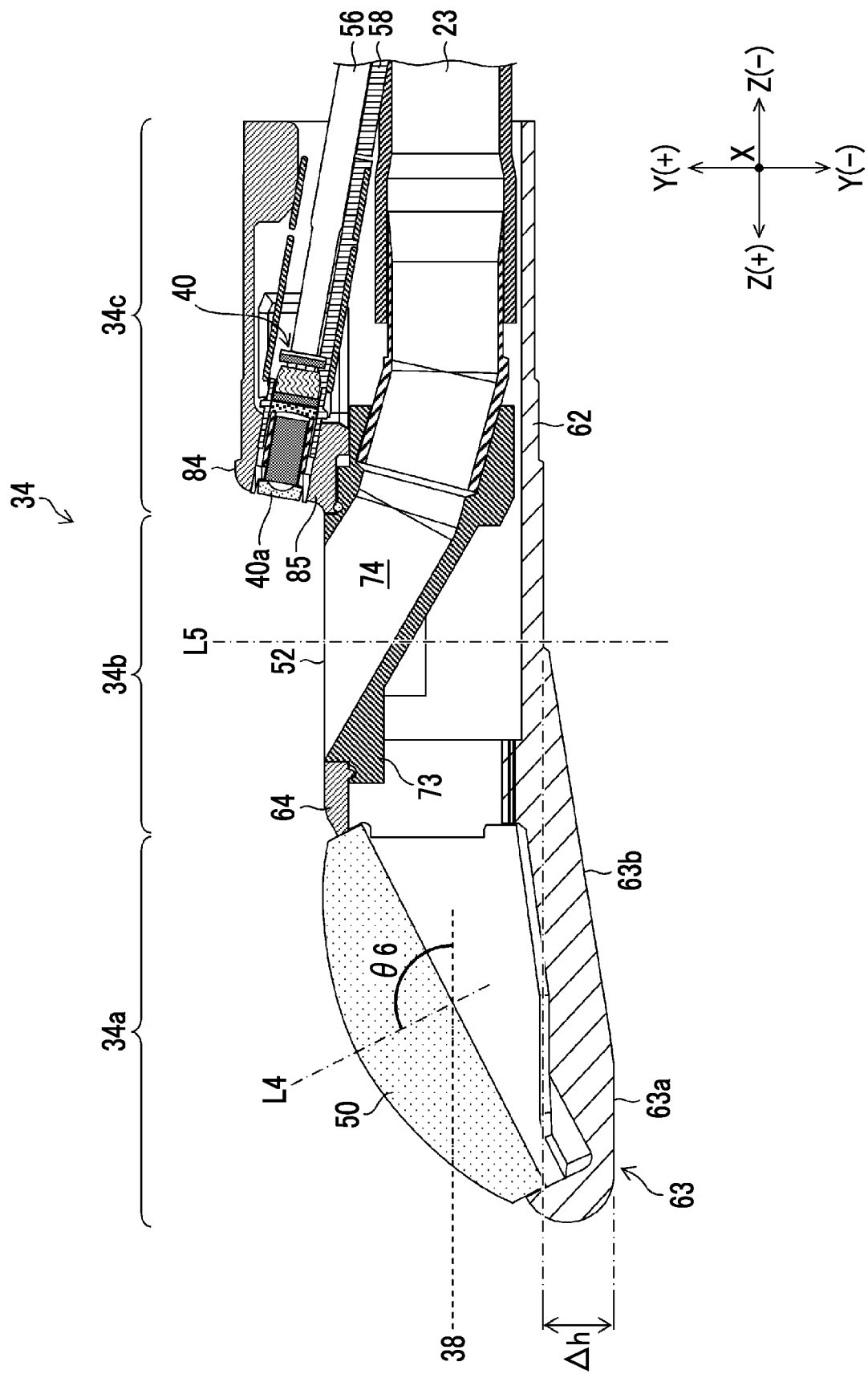
FIG. 12 is a sectional view of a distal end hard part of an endoscope of a sixth embodiment.

FIG. 12 is a sectional view of the distal end hard part 34 of the endoscope 1 of the sixth embodiment. As shown in FIG. 12, in the distal end hard part 34 of the sixth embodiment, a protruding portion 63 that protrudes to the Y(−) direction side with respect to the body part 34c in a case of being viewed from the X direction side is formed. Specifically, the protruding portion 63 is formed from an opening region of the outlet port 52 in the outlet port forming part 34b of the distal end hard part 34, for example, the center of the outlet port 52 indicated by a center line L5 to the distal end side of the ultrasonic attachment part 34a.

The protruding portion 63 may be formed from any position of the opening region of the outlet port 52 to the distal end side of the ultrasonic attachment part 34a. The protruding portion 63 may be formed only in the ultrasonic attachment part 34a. That is, the protruding portion 63 may be formed in at least the ultrasonic attachment part 34a.

A height Δh of the protruding portion 63 is set to, for example, 2.7 mm. The protruding portion 63 is provided in at least the ultrasonic attachment part 34a in this way, whereby it is possible to tilt forward only the ultrasound transducer 50 to the Y(−) direction side at an angle θ6 (θ6≥110°) with respect to the longitudinal axis 38 without tilting forward the distal end part or the whole distal end hard part 34 to the Y(−) direction side with respect to the longitudinal axis 38. As a result, the proximal end part of the ultrasound transducer 50 is easily brought into contact with the bronchial wall surface.

Here, in a case where the distal end part or the whole distal end hard part 34 is tilted forward, while the insertability of the distal end hard part 34 (insertion part 12) is reduced, in the sixth embodiment, only the ultrasound transducer 50 is tilted forward, resulting in improvement of insertability. As a result, the insertability of the distal end hard part 34 (insertion part 12) into a body of a patient is improved.

The protruding portion 63 has inclined surfaces 63a and 63b of two stages having different inclination angles with respect to the longitudinal axis 38 from a proximal end side toward a distal end side of the protruding portion 63 in a case where the distal end hard part 34 is viewed from the X direction side. The inclination angle of the inclined surface 63a on the distal end side between the inclined surfaces 63a and 63b is smaller than the inclination angle of the inclined surface 63b on the proximal end side.

The inclined surfaces 63a and 63b as planar portions are formed in the protruding portion 63, whereby a contact area of the protruding portion 63 and a wall surface in a body, such as a bronchial wall surface, is increased, and contact pressure against the wall surface in the body by the protruding portion 63 can be reduced. In the sixth embodiment, since the inclined surface 63a on the distal end side is formed substantially parallel with the longitudinal axis 38, contact pressure against the wall surface in the body by the protruding portion 63 can be further reduced. As a result, a burden on a patient can be reduced.

In the sixth embodiment, while the inclined surfaces 63a and 63b of two stages are formed in the protruding portion 63, inclined surfaces of three stages or more may be formed. Even in this case, the inclination angle of each inclined surface gradually decreases toward the distal end side of the protruding portion 63. It is preferable that the inclined surface on the most distal end side is formed substantially parallel with the longitudinal axis 38.

Figure 13:
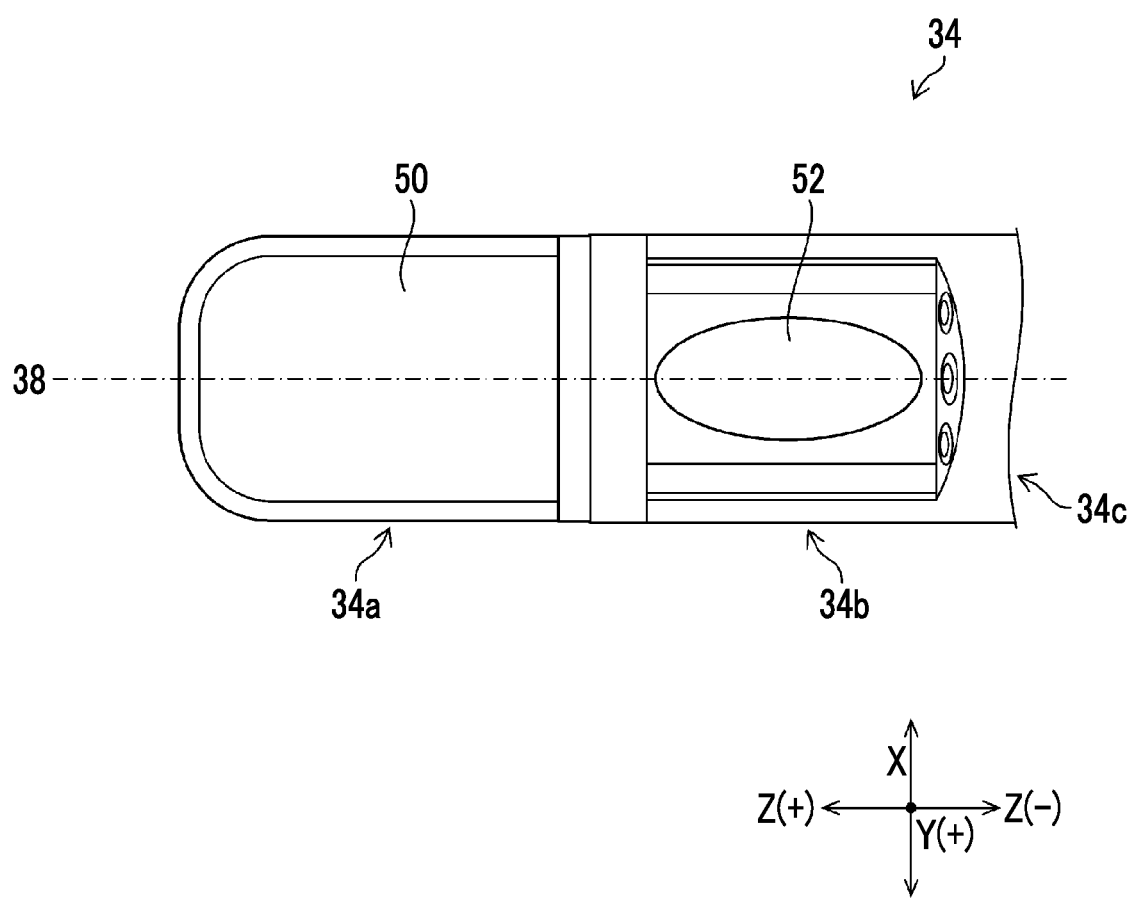
FIG. 13 is a top view of the distal end hard part of the endoscope of the first embodiment to the sixth embodiment.
Figure 14:
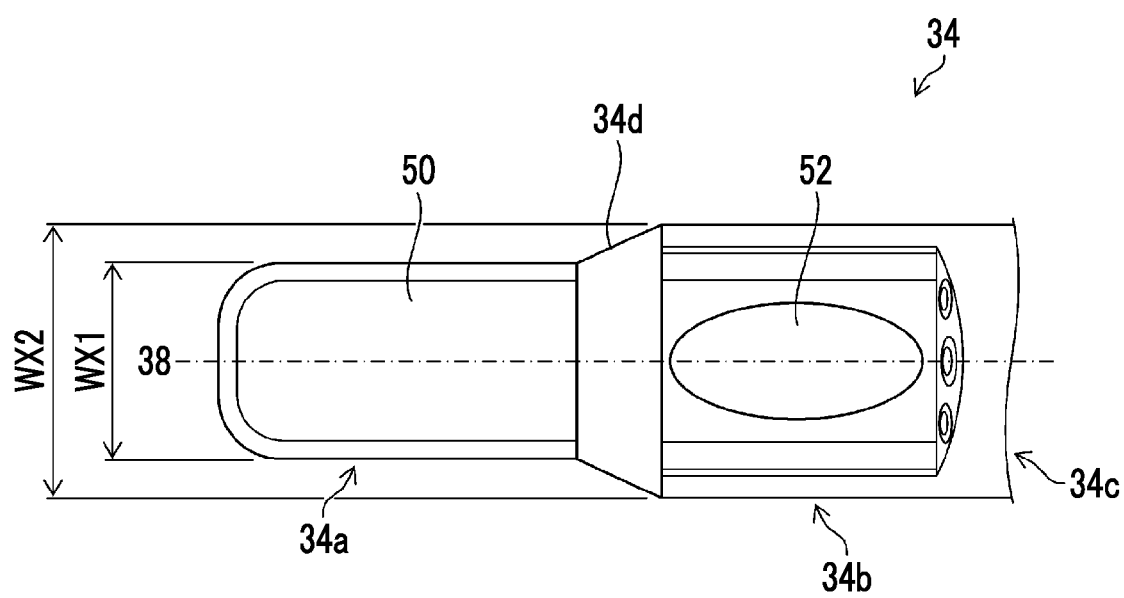
FIG. 14 is a top view showing a modification example of the distal end hard part of the endoscope of the sixth embodiment.

FIG. 13 is a top view of the distal end hard part 34 of the endoscope 1 of the first embodiment to the sixth embodiment. FIG. 14 is a top view showing a modification example of the distal end hard part 34 of the endoscope 1 of the sixth embodiment. As shown in FIG. 13, in the distal end hard part 34 of each embodiment described above, the ultrasonic attachment part 34a and the outlet port forming part 34b have the substantially same width in the X direction in a case of being viewed from the Y(+) direction side (corresponding to a first direction side of the present invention).

In contrast, as shown in FIG. 14, in the modification example of the distal end hard part 34 of the sixth embodiment, a width WX1 (for example, 5.7 mm) in the X direction of the ultrasonic attachment part 34a is formed to be smaller than a width WX2 (for example, 6.4 mm) in the X direction of the outlet port forming part 34b in a case of being viewed from the Y(+) direction side. The width WX1 is made smaller than the width WX2, whereby an inclined surface 34d (corresponding to a connecting inclined surface of the present invention) that connects the proximal end side of the ultrasonic attachment part 34a and the distal end side of the outlet port forming part 34b is formed in the distal end hard part 34.

In this way, the width WX1 of the ultrasonic attachment part 34a is narrowed, whereby only the ultrasonic attachment part 34a can be reduced in size and can be inserted into a bronchus periphery. The inclined surface 34d is formed between the ultrasonic attachment part 34a and the outlet port forming part 34b, whereby it is possible to ensure insertability even in a case where only the ultrasonic attachment part 34a is reduced in size.

Seventh Embodiment

Next, a distal end hard part 34 of an endoscope 1 of a seventh embodiment of the present invention will be described. In each embodiment described above, since a balloon, a protrusion for attachment thereof, a groove, and a pipe line are not provided in the distal end hard part 34, a reduction in size and a reduction in length in the Z direction of the distal end hard part 34 are achieved. As a result, in each embodiment described above, improvement of the insertability of the insertion part 12, reduction of a burden on a patient, and assurance of sterilizability in a sterilizer that performs washing and disinfection are realized. Note that, in this case, the puncture needle 100 led out from the outlet port 52 may approach the ultrasound transducer 50.

Accordingly, the distal end hard part 34 of the seventh embodiment has a shape capable of securing a clearance between the puncture needle 100 led out from the outlet port 52 and the ultrasound transducer 50. Since the distal end hard part 34 of the seventh embodiment has essentially the same configuration as the distal end hard part 34 of each embodiment described above, the same elements in function or configuration as those in each embodiment described above are represented by the same reference numerals, and description thereof will not be repeated. Furthermore, description of the same effects as in each embodiment described above will also not be repeated.

Figure 15:
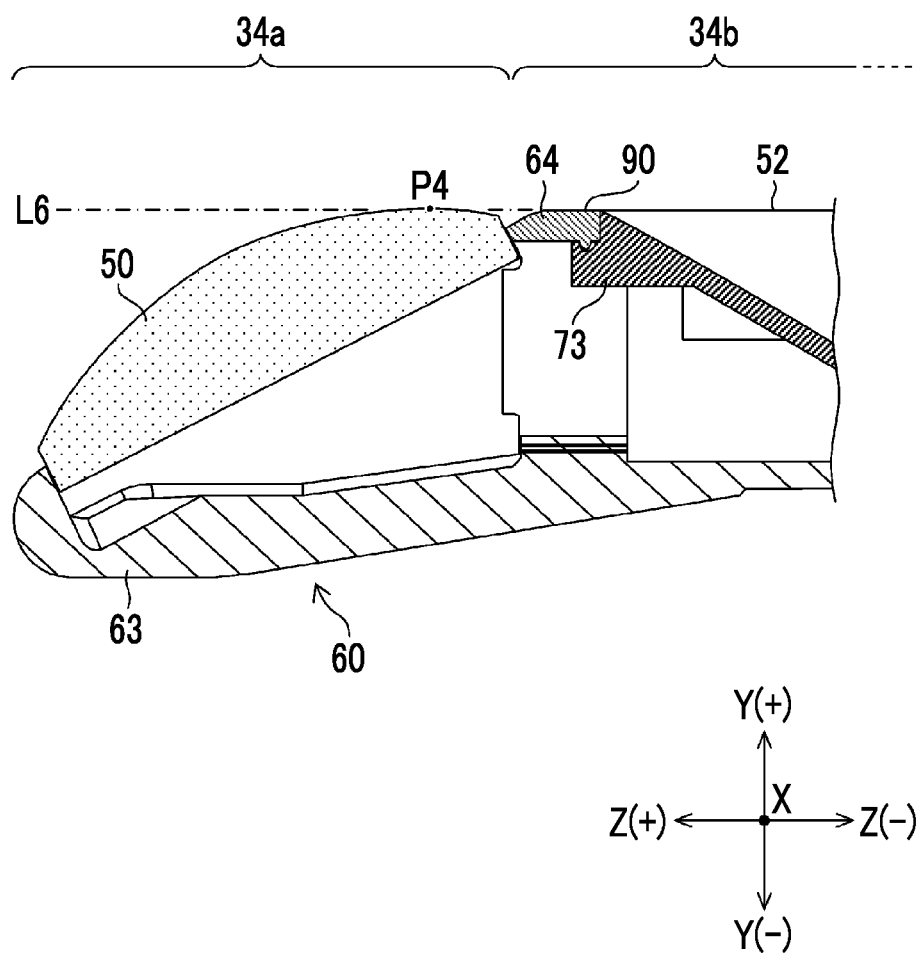
FIG. 15 is a sectional view of a distal end hard part of an endoscope of a seventh embodiment.

FIG. 15 is a sectional view of the distal end hard part 34 of the endoscope 1 of the seventh embodiment. As shown in FIG. 15, in the distal end hard part 34 of the seventh embodiment, a position in the Y direction of the outlet port 52 and a position of an apex P4 on the Y(+) direction side of the ultrasound transducer 50 are aligned as indicated by a one-dot chain line L6 in the drawing in a case of being viewed from the X direction side. As a result, since the distal end of the puncture needle 100 led out from the outlet port 52 passes through a position on the Y(+) direction side with respect to the apex P4 of the ultrasound transducer 50, a clearance is reliably secured between the distal end of the puncture needle 100 and the ultrasound transducer 50. As a result, it is possible to reliably prevent interference of the puncture needle 100 with the ultrasound transducer 50.

[Other]

In each embodiment described above, although the endoscope 1 in which a balloon pipe line is not provided in the distal end hard part 34 has been described as an example, the present invention can also be applied to an endoscope 1 in which a balloon pipe line is provided in the distal end hard part 34.

In each embodiment described above, although the distal end hard part 34 is configured by combining the ultrasound block component 60, the channel block component 70, and the optical system block component 80, the distal end hard part 34 may be configured with four or more block components. A plurality of or all block components may be formed integrally. Therefore, the present invention can be applied to various distal end hard parts 34 having the ultrasonic attachment part 34a, the outlet port forming part 34b, and the body part 34c.

In each embodiment described above, although the outlet port 52 is provided between the ultrasound transducer 50 and the stepped surface 85 (observation window 40a) in a case where the distal end hard part 34 is viewed from the X direction side, the outlet port 52 may be provided on the proximal end side of the stepped surface 85 (observation window 40a).

In the embodiments described above, although the endoscope 1 (ultrasonic bronchoscope) that performs a test of a lymph node of a bronchus has been described as an example, the endoscope 1 of the present invention is not limited to an ultrasonic bronchoscope, and can also be applied to an ultrasonic digestive endoscope. That is, the present invention can also be applied to various ultrasonic endoscopes and to the distal end hard part 34 (distal end unit) provided on the distal end side of the insertion part 12. The type of the treatment tool that is used in the ultrasonic endoscope is not limited to the puncture needle 100, and various known treatment tools can be used. The present invention can also be applied to an ultrasonic endoscope that does not comprise the observation optical system 40 and the illumination optical system 44, and to a distal end hard part thereof.

EXPLANATION OF REFERENCES

1: ultrasonic endoscope (endoscope)
10: operating part
12: insertion part
14: universal cord
16: angle lever
22: suction button
23: treatment tool insertion channel
24: treatment tool inlet port
30: soft part
32: bendable part
34: distal end hard part
34a: ultrasonic attachment part
34b: outlet port forming part
34c: body part
34d: inclined surface
38: longitudinal axis
40: observation optical system
40a: observation window
40b: lens system
40c: imaging element
44: illumination optical system
44a: illumination window
50: ultrasound transducer
52: outlet port
54: signal cable
56: signal cable
58: light guide
60: ultrasound block component
62: optical system block component attachment part
63: protruding portion
63a: inclined surface
63b: inclined surface
64: locking portion
65: attachment part opening
66: guide portion
70: channel block component
71: opening forming surface
72: flange surface
73: locked portion
74: in-block pipe line
74a: first pipe line
74b: second pipe line
80: optical system block component
81: channel block component attachment portion
81a: plane
81b: support surface
82: optical system storage portion
84: convex surface
85: stepped surface
90: continuous plane
100: puncture needle
200: lymph node
C: center point
DA: diameter
d: interval
L2A: center line
L2B: center line
L4: center line
L5: center line
L6: one-dot chain line
LT: tangent line
P1: tangent point
P2: tangent point
P3: intersection
P4: apex
R1: irradiation range
W: range
WX1, WX2: width
Δh: height
θ1: effective angle
θ2: angle
θ3: angle
θ4: angle
θ5: angle
θ6: angle

What is claimed is:

1. An ultrasonic endoscope comprising:
a distal end part body provided on a distal end side of an insertion part; and
an ultrasound transducer provided on a distal end side of the distal end part body,
wherein an outer peripheral surface of the distal end part body includes
a first surface that is provided on a proximal end side of the ultrasound transducer and that extends along a longitudinal axis of the insertion part,
a second surface that is provided on a proximal end side of the first surface and that extends along the longitudinal axis, the second surface being positioned on a one direction side of a first direction perpendicular to the longitudinal axis with respect to the first surface, and
a stepped surface that connects the proximal end side of the first surface and a distal end side of the second surface, and
in a case where a direction perpendicular to both the longitudinal axis and the first direction is referred to as a second direction, an angle indicating an irradiation range of an ultrasonic wave emitted from the ultrasound transducer in a case where the distal end part body is viewed from a second direction side is referred to as an effective angle, and an intersection of a tangent line in contact with the ultrasound transducer and in contact with the stepped surface at a position closest to the one direction side and the ultrasound transducer is referred to as a first intersection, the first intersection is included in a range of 1/3 on a proximal end side of the effective angle.

2. The ultrasonic endoscope according to claim 1, further comprising:
an outlet port that is provided in the outer peripheral surface of the distal end part body and that is opened on the one direction side, and from which a treatment tool is led out;
a pipe line that is connected to the outlet port in the distal end part body and into which the treatment tool is inserted; and
an observation window of an observation optical system provided in the stepped surface,
wherein a second intersection that is an intersection of a center line of a distal end part of the pipe line connected to the outlet port and the tangent line is positioned on a proximal end side of the distal end part body with respect to the first intersection in a case where the distal end part body is viewed from the second direction side.

3. The ultrasonic endoscope according to claim 2,
wherein the second intersection is positioned between the ultrasound transducer and the stepped surface.

4. The ultrasonic endoscope according to claim 1, further comprising:

an outlet port that is provided in the outer peripheral surface of the distal end part body and that is opened on the one direction side, and from which a treatment tool is led out; and a pipe line that is connected to the outlet port in the distal end part body and into which the treatment tool is inserted, wherein an angle between the longitudinal axis and a distal end part of the pipe line is 20° to 35° in a case where the distal end part body is viewed from the second direction side.

5. The ultrasonic endoscope according to claim 2,
wherein the distal end part of the pipe line has a first distal end part that is connected to the outlet port, and a second distal end part that is provided on a proximal end side of the first distal end part, and in a case where the distal end part body is viewed from the second direction side, a first angle between the longitudinal axis and the first distal end part is 20° to 35°, and a second angle between the longitudinal axis and the second distal end part is 5° to 20° and is an angle smaller than the first angle.

6. The ultrasonic endoscope according to claim 2,
wherein an angle between a center line of the effective angle and the distal end part of the pipe line is 15° to 60° in a case where the distal end part body is viewed from the second direction side.

7. The ultrasonic endoscope according to claim 1,
wherein an observation window of an observation optical system is provided in the stepped surface, and
the ultrasound transducer is included in a visual field range of the observation optical system.

8. The ultrasonic endoscope according to claim 7,
wherein a center point of the observation window is positioned on the one direction side with respect to the ultrasound transducer in a case where the distal end part body is viewed from the second direction side.

9. The ultrasonic endoscope according to claim 1,
wherein an observation window of an observation optical system and an illumination window of an illumination optical system are provided in the stepped surface.

10. The ultrasonic endoscope according to claim 1, further comprising:
an outlet port that is opened in the first surface and from which a treatment tool is led out; and
an observation window of an observation optical system provided in the stepped surface.

11. The ultrasonic endoscope according to claim 1,
wherein the distal end part body includes
an ultrasonic attachment part to which the ultrasound transducer is attached,
a first surface forming part that is provided on a proximal end side of the ultrasonic attachment part and that has the first surface,
a body part that is provided on a proximal end side of the first surface forming part and that has the second surface, and
a protruding portion that is provided in at least the ultrasonic attachment part and that protrudes to the other direction side opposite to the one direction side with respect to the body part.

12. The ultrasonic endoscope according to claim 11,
wherein an outlet port from which a treatment tool is led out is opened in the first surface, and
the protruding portion is formed from an opening region of the outlet port to a distal end side of the ultrasonic attachment part in a case where the distal end part body is viewed from the second direction side.

13. The ultrasonic endoscope according to claim 11,
wherein the protruding portion has inclined surfaces of two stages or more having different inclination angles with respect to the longitudinal axis from a proximal end side toward a distal end side of the protruding portion in a case where the distal end part body is viewed from the second direction side, and
the inclination angles of the inclined surfaces gradually decrease toward the distal end side of the protruding portion.

14. The ultrasonic endoscope according to claim 1,
wherein an outlet port from which a treatment tool is led out is opened in the first surface, and
a position in the first direction of the outlet port and a position of an apex in the first direction of the ultrasound transducer are aligned in a case where the distal end part body is viewed from the second direction side.

15. The ultrasonic endoscope according to claim 1,
wherein the distal end part body includes
an ultrasonic attachment part to which the ultrasound transducer is attached,
a first surface forming part that is provided on a proximal end side of the ultrasonic attachment part and that has the first surface and an outlet port of a treatment tool formed in the first surface, and
a body part that is provided on a proximal end side of the first surface forming part and that has the second surface, and
a width in the second direction of the ultrasonic attachment part is formed to be smaller than a width in the second direction of the first surface forming part in a case where the distal end part body is viewed from a first direction side.

16. The ultrasonic endoscope according to claim 15, further comprising:
a connecting inclined surface that connects the proximal end side of the ultrasonic attachment part and a distal end side of the first surface forming part.

17. A distal end unit of an ultrasonic endoscope including a distal end part body provided on a distal end side of an insertion part of the ultrasonic endoscope, and an ultrasound transducer provided on a distal end side of the distal end part body,
wherein an outer peripheral surface of the distal end part body includes
a first surface that is provided on a proximal end side of the ultrasound transducer and that extends along a longitudinal axis of the insertion part,
a second surface that is provided on a proximal end side of the first surface and that extends along the longitudinal axis, the second surface being positioned on a one direction side of a first direction perpendicular to the longitudinal axis with respect to the first surface, and
a stepped surface that connects the proximal end side of the first surface and a distal end side of the second surface, and
in a case where a direction perpendicular to both the longitudinal axis and the first direction is referred to as a second direction, an angle indicating an irradiation range of an ultrasonic wave emitted from the ultrasound transducer in a case where the distal end part body is viewed from a second direction side is referred to as an effective angle, and an intersection of a tangent line in contact with the ultrasound transducer and in contact with the stepped surface at a position closest to the one direction side and the ultrasound transducer is referred to as a first intersection, the first intersection is included in a range of 1/3 on a proximal end side of the effective angle.

* * * * *